United States Patent
Teschner et al.

(10) Patent No.: US 10,125,189 B2
(45) Date of Patent: *Nov. 13, 2018

(54) METHOD TO PRODUCE A HIGHLY CONCENTRATED IMMUNOGLOBULIN PREPARATION FOR SUBCUTANEOUS USE

(71) Applicants: Baxalta Incorporated, Bannockburn, IL (US); Baxalta GmbH, Zug (CH)

(72) Inventors: Wolfgang Teschner, Vienna (AT); Harald Arno Butterweck, Vienna (AT); Azra Pljevljakovic, Vienna (AT); Theresa Friederike Bauer, Vienna (AT); Bernhard Koelbl, Achau (AT); Hans-Peter Schwarz, Vienna (AT); Nebojsa Nikolic, Vienna (AT); Gerhard Poelsler, Vienna (AT); Johanna Kindermann, Maria Enzersdorf (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 246 days.

This patent is subject to a terminal disclaimer.

(21) Appl. No.: 14/855,686

(22) Filed: Sep. 16, 2015

(65) Prior Publication Data

US 2016/0244512 A1 Aug. 25, 2016

Related U.S. Application Data

(60) Division of application No. 13/949,565, filed on Jul. 24, 2013, now Pat. No. 9,175,068, which is a continuation of application No. 12/789,345, filed on May 27, 2010, now Pat. No. 8,546,548.

(60) Provisional application No. 61/181,606, filed on May 27, 2009.

(51) Int. Cl.
| | |
|---|---|
| *C07K 16/06* | (2006.01) |
| *B01D 61/14* | (2006.01) |
| *C07K 16/18* | (2006.01) |
| *A61K 39/395* | (2006.01) |
| *C07K 16/00* | (2006.01) |
| *A61K 39/00* | (2006.01) |

(52) U.S. Cl.
CPC ........ *C07K 16/18* (2013.01); *A61K 39/39591* (2013.01); *B01D 61/142* (2013.01); *B01D 61/145* (2013.01); *C07K 16/00* (2013.01); *C07K 16/065* (2013.01); *A61K 2039/505* (2013.01); *A61K 2039/54* (2013.01); *B01D 2315/16* (2013.01); *C07K 2317/10* (2013.01); *C07K 2317/21* (2013.01)

(58) Field of Classification Search
None
See application file for complete search history.

(56) References Cited

U.S. PATENT DOCUMENTS

| 4,136,094 | A | 1/1979 | Condie |
|---|---|---|---|
| 5,122,373 | A | 6/1992 | Eibl et al. |
| 5,177,194 | A | 1/1993 | Sarno et al. |
| 5,886,154 | A | 3/1999 | Lebing et al. |
| 6,069,236 | A | 5/2000 | Burnout-Radosevich et al. |
| 6,093,324 | A | 7/2000 | Bertolini et al. |
| 6,835,379 | B2 | 12/2004 | Andersson et al. |
| 7,138,120 | B2 | 11/2006 | Laursen et al. |
| 7,186,410 | B2 | 3/2007 | Chtourou et al. |
| 7,553,938 | B2 | 6/2009 | Buchacher et al. |
| 8,546,548 | B2 * | 10/2013 | Teschner .......... A61K 39/39591 |
| | | | 530/412 |
| 8,772,461 | B2 | 7/2014 | Gonzalez et al. |
| 9,175,068 | B2 * | 11/2015 | Teschner .......... A61K 39/39591 |
| 2006/0051347 | A1 * | 3/2006 | Winter .............. A61K 39/39591 |
| | | | 424/133.1 |
| 2009/0148463 | A1 | 6/2009 | Reipert et al. |
| 2011/0213126 | A1 | 9/2011 | Gonzalez et al. |

FOREIGN PATENT DOCUMENTS

| CN | 1157572 A | 8/1997 |
|---|---|---|
| CN | 1311797 A | 9/2001 |
| CN | 101279246 A | 10/2008 |
| EP | 0 363 896 A2 | 4/1990 |
| GB | 1 344 340 | 9/1972 |
| SE | 348 942 | 9/1972 |
| WO | WO 00/67789 | † 11/2000 |
| WO | WO 00/67789 A1 | 11/2000 |
| WO | WO 2005/023867 A1 | 3/2005 |
| WO | WO 2005/073252 A1 | † 8/2005 |

(Continued)

OTHER PUBLICATIONS

Winter et al. "Cascade ultrafiltration bioreactor-separator system for continuous production of F(ab')2 fragment from immunoglobulin G" J. Membrane Science 351 (2010) 96-103 (Year: 2010).*
Barandun, S. et al., "Intravenous Administration of Human γ-Globulin," *Vox Sanguinis*, 1962, pp. 157-174, vol. 7.
Bee, W.H. et al., "Effects of Recombinant Human Hyaluronidase (rHuPH20) on Subcutaneous Administration of 10% and 20% IgC in Yucatan Mini Pigs," *J. Allergy Clin. Immunol.*, Feb. 2010, 2 pages (p. Abstracts AB139), Abstract No. 547, vol. 125, No. 2, Suppl 2.
Cohn, E.J. et al., "Preparation and Properties of Serum and Plasma Proteins. IV. A System for the Separation into Fractions of the Protein and Lipoprotein Components of Biological Tissues and Fluids," *J. Am. Chem. Soc.*, Mar. 1946, pp. 459-475, vol. 68, No. 3.
Cummins, L.M. et al., "Preparation and Characterization of an Intravenous Solution of IgG From Human Immunodeficiency Virus-Seropostive Donors," *Blood*, Mar. 1, 1991, vol. 77, No. 5, pp. 1111-1117.

(Continued)

*Primary Examiner* — Daniel E Kolker
*Assistant Examiner* — James L Rogers
(74) *Attorney, Agent, or Firm* — Morgan, Lewis & Bockius LLP

(57) ABSTRACT

The present invention relates to a new and improved method for preparing a highly concentrated immunoglobulin composition from pooled plasma for subcutaneous injection. A composition comprising 20% or more immunoglobulin suitable for subcutaneous use is also described.

18 Claims, 7 Drawing Sheets

(56) References Cited

FOREIGN PATENT DOCUMENTS

| WO | WO 2006/031560 A2 | 3/2006 |
|---|---|---|
| WO | WO 2009/129226 A1 | 10/2009 |

OTHER PUBLICATIONS

Deville-Bonne, D. et al., "Ordered Disruption of Subunit Interfaces during the Stepwise Reversible Dissociation of *Escherichia coli* Phosphofructokinase with KSCN," *Biochemistry*, 1989, vol. 28, pp. 1917-1922.

Falksveden, L.-G. et al., "Ion Exchange and Polyethylene Glycol Precipitation of Immunoglobulin G," in *Methods of Plasma Protein Fractionation*, Curling, J.M. ed., 1980, pp. 93-103, Academic Press, New York, NY.

Hemming, V.G., "Use of Intravenous Immunoglobulins for Prophylaxis or Treatment of Infectious Diseases," *Clinical and Diagnostic Laboratory Immunology*, Sep. 2001, vol. 8, No. 5, pp. 859-863.

Hermann, C. et al., "Analysis of Fc-Receptor-Mediated Activities of New IgG Products Using a Novel THP-1 Cell-based Assay," *J. Allergy Clin. Immunol.*, Feb. 2010, 2 pages (p. Abstracts AB79), Abstract No. 312, vol. 125, No. 2, Suppl 1.

Hofmeister, Y. et al., "Human IgG Subclasses: In Vitro Neutralization of and In Vivo Protection against West Nile Virus," *Journal of Virology*, Feb. 2011, pp. 1896-1899, vol. 85, No. 4.

Knezevic-Maramica, I. et al., "Intravenous immune globulins: an update for clinicians," *Transfusion*, Oct. 2003, vol. 43, pp. 1460-1480.

Koblet, H. et al., "Turnover of Standard-Gammaglobulin, pH-4-Gammaglobulin and Pepsin Desaggregated Gammaglobulin and Clinical Implications," *Vox Sanguinis*, 1967, pp. 93-102, vol. 13.

International Search Report dated Jan. 26, 2011, for International Application No. PCT/US2010/036430 filed on May 27, 2010, 1 page.

Kolarich, D. et al., "Glycoproteomic characterization of butyrylcholinesterase from human plasma," *Proteomics*, 2008, vol. 8, pp. 254-263.

Kreil, T.R. et al., "Development of a New 10% Liquid, Triple Virus Reduced Intra-venous Immune-Globulin Product, New Generation IGIV," *J. Allergy Immunol.*, Feb. 2004, p. S128 Abstracts, Abstract No. 410.

Kreil, T.R. et al., "Pathogen Safety Profile of a New 10% Liquid, Triple Virus Reduced Intravenous Immune Globulin Product, New Generation IGIV (NG IGIV)—Further Studies," *J. Allergy Clin. Immunol.*, Feb. 2005, p. S156 Abstracts, Abstract No. 623.

Kreil, T.R. et al., "Removal of small nonenveloped viruses by antibody-enhanced nanofiltration during the manufacture of plasma derivatives," *Transfusion*, Jul. 2006, pp. 1143-1151, vol. 46.

Le Bras, G. et al., "Urea-Induced Inactivation, Dissociation, and Unfolding of the Allosteric Phosphofructokinase from *Escherichia coli*," *Biochemistry*, 1989, vol. 28, No. 17, pp. 6836-6841.

Lebing, W. et al., "Properties of a new intravenous immunoglobulin (IGIV-C, 10%) produced by virus inactivation with caprylate and column chromatography," *Vox Sanguinis*, 2003, pp. 193-201, vol. 84.

Leesch, V.W. et al., "30-Day Pharmacokinetic Evaluation of IV versus Subcutaneous Administration of Immunoglobulin with and without Recombinant Human Hyaluronidase in Dogs," *J. Allergy Clin. Immunol.*, Feb. 2009, p. S10 Abstracts, Abstract No. 24.

Muchitsch, E.-M. et al., "In vivo Effect of $\alpha_1$-Acid Glycoprotein on Experimentally Enhanced Capillary Permeability in Guinea-Pig Skin," *Arch. Int. Pharmacodyn.*, 1996, vol. 331, pp. 312-321.

Mumford, H. et al., "Efficacy and physiological effects of human butyrylcholinesterase as a post-exposure therapy against percutaneous poisoning by VX in the guinea-pig," *Chemico-Biological Interactions*, 2010, vol. 187, pp. 304-308.

Olas, K. et al., "Pro-Inflammatory and Anti-Inflammatory Activities of Human Plasma-Derived Serum IgA," *Immunology 2004, Genomic Issues, Immune System Activation and Allergy, Collection of Free Papers Presented at the 12th International Congress of Immunology and 4th Annual Conference of FOCIS*, 2004, Montreal, Canada, Jul. 18-23, 2004, pp. 531-535.

Olas, K. et al., "Immunomodulatory properties of human serum immunoglobulin A: anti-inflammatory and pro-inflammatory activities in human monocytes and peripheral blood mononuclear cells," *Clinical and Experimental Immunology*, 2005, pp. 478-490, vol. 140.

Olas, K. et al., "Natural anti-amyloid beta antibodies in intravenous immunoglobulin prevent amyloid beta-induced neurotoxicity in vitro," *Immunology*, 2008, p. 19, Abstract No. 3.5, vol. 125, Suppl 1.

Oncley, J.L et al., "The Separation of the Antibodies, Isoagglutinins, Prothrombin, Plasminogen and $\beta_1$-Lipoprotein into Subtractions of Human Plasma," *J. Am. Chem. Soc.*, Feb. 1949, pp. 541-550, vol. 71.

Peters, F. et al., "DIADEM—A System for the Interactive Data Acquisition and Processing in an Analytical Laboratory," *Computer Programs in Biomedicine*, 1979, vol. 10, pp. 125-132.

Poelsler, G. et al., "A new liquid intravenous immunoglobulin with three dedicated virus reduction steps: virus and prion reduction capacity," *Vox Sanguinis*, 2007, pp. 1-9.

Reipert, B.M. et al., "Evaluating the Fc-Function of Intravenous Immunoglobulin Products by Flow Cytometry," *J. Allergy Clin. Immunol.*, Feb. 2004, p. S214 Abstracts, Abstract No. 751.

Reipert, B.M. et al., "Fc function of a new intravenous immunoglobulin product: IGIV 10% triple virally inactivated solution," *Vox Sanguinis*, 2006, pp. 256-263, vol. 91.

Serre, M-C. et al., "Specific Suppression of Heterotropic Interactions in Phosphofructokinase by the Mutation of Leucine 178 into Tryptophan," *The Journal of Biological Chemistry*, Jul. 25, 1990, vol. 265, No. 21, pp. 12146-12148.

Tanaka, K. et al., "High quality human immunoglobulin G purified from Cohn fractions by liquid chromatography," *Brazilian Journal of Medical and Biological Research*, 2000, pp. 27-30, vol. 33, No. 1.

Teschner, W. et al., "Intermediates on the Folding Pathway of Octopine Dehydrogenase from *Pecten jacobaeus*," *Biochemistry*, 1987, vol. 26, pp. 2791-2796.

Teschner, W. et al., "Intermediates on the Reassociation Pathway of Phosphofructokinase I from *Escherichia coli*," *Biochemistry*, 1989, vol. 28, pp. 1912-1916.

Teschner, W. et al., "A carboxypeptidase Y pulse method to study the accessibility of the C-terminal end during the refolding of ribonuclease A," *Biochem. J.*, 1989, vol. 260, pp. 583-587.

Teschner, W. et al., "Introduction by site-directed mutagenesis of a tryptophan residue as a fluorescent probe for the folding of *Escherichia coli* phosphofructokinase," *Biochimie*, 1990, vol. 72, pp. 403-406.

Teschner, W. et al., "Enzymatic properties, renaturation and metabolic role of mannitol-1-phosphate dehydrogenase from *Escherichia coli*," *Biochimie*, 1990, vol. 72, pp. 33-40.

Teschner, W. et al., "Fructose-6-phosphate modifies the pathway of the urea-induced dissociated of the allosteric phosphfructokinase from *Escherichia coli*," *FEBS*, Jul. 1990, vol. 267, No. 1, pp. 96-98.

Teschner, IV, W. et al., "Preclinical Characterization of a New Liquid 'Immune Globulin Intravenous (Human), 10% Triple Virally Reduced Solution' (IGIV, 10%TVR)," *J. Allergy Clin. Immunol.*, Feb. 2004, 2 pages, (p. Abstracts S45), Abstract No. 79, vol. 113, No. 2, Suppl 1.

Teschner, W. et al., "A new liquid, intravenous immunoglobulin product (IGIV 10%) highly purified by a state-of-the-art process," *Vox Sanguinis*, 2007, vol. 92, pp. 42-55.

Van Reis, R. et al., "Bioprocess membrane technology," *Journal of Membrane Science*, 2007, vol. 297, pp. 16-50.

Weber, A. et al., "Intravenous Immunoglobulin (IVIG) Gammagard Liquid Contains Anti-Rage IGG and SLRP," *Alzheimer's & Dementia: The Journal of the Alzheimer's Association*, Jul. 2009, 3 pages (p. P416), Abstract No. P3-248, vol. 5, No. 4, Suppl.

Weber, A. et al., "Biochemical, molecular and preclinical characterization of a double-virus-reduced human butyrylcholinesterase preparation designed for clinical use," *Vox Sanguinis*, 2011, vol. 100, pp. 285-297.

(56) References Cited

OTHER PUBLICATIONS

Zettlmeissl, G. et al., "Isolation, physicochemical properties, and folding of octopine dehydrogenase from *Pecten jacobaeus*," *Eur. J. Biochem.*, 1984, vol. 143, pp. 401-407.

\* cited by examiner
† cited by third party

METHOD TO PRODUCE A HIGHLY CONCENTRATED IMMUNOGLOBULIN PREPARATION FOR SUBCUTANEOUS USE

CROSS-REFERENCES TO RELATED APPLICATIONS

This application is a divisional of U.S. patent application Ser. No. 13/949,565, filed Jul. 24, 2013 (now issued as U.S. Pat. No. 9,175,068), which is a continuation of U.S. patent application Ser. No. 12/789,345, filed May 27, 2010 (now issued as U.S. Pat. No. 8,546,548), which claims the benefit of U.S. Provisional Application No. 61/181,606 filed May 27, 2009, which are expressly incorporated herein by reference in their entirety for all purposes.

BACKGROUND OF THE INVENTION

Immune globulin products from human plasma were first used in 1952 to treat immune deficiency. Initially, intramuscular or subcutaneous administration of IgG were the methods of choice. For injecting larger amounts of IgG necessary for effective treatment of various diseases, however, the intravenous administrable products with lower concentrated IgG (50 mg/mL) were developed. Usually intravenous immunoglobulin (IVIG), contains the pooled immunoglobulin G (IgG) immunoglobulins from the plasma of more than a thousand blood donors. Typically containing more than 95% unmodified IgG, which has intact Fc-dependent effector functions, and only trace amounts of immunoglobulin A (IgA) or immunoglobulin M (IgM), IVIGs are sterile, purified IgG products primarily used in treating three main categories of medical conditions: 1. immune deficiencies such as X-linked agammaglobulinemia, hypogammaglobulinemia (primary immune deficiencies), and acquired compromised immunity conditions (secondary immune deficiencies), featuring low antibody levels; 2. inflammatory and autoimmune diseases; and 3. acute infections.

A number of IVIG commercial suppliers provide a variety of IVIG products. Compared to the older lyophilized IVIG products containing only 50 mg/mL protein in the solution after re-dissolving, the latest developments are 100 mg/mL ready-for-use sterile, liquid preparation of highly purified and concentrated human IgG antibodies. Since IgG products such as IVIGs are manufactured from pooled human plasma, pathogen contamination (especially viruses known to cause various diseases in human) from donor blood is a serious concern in the production process. Another important consideration in IgG products is their stability during storage, especially as ready-for-use preparations. Compared to IVIG, subcutaneously administrable immunoglobulin preparations have the advantages of home-care treatment possibility and less side effects. To reduce the disadvantage of the small injection volume per site, a higher concentrated IgG (e.g., containing 200 mg/mL instead of 100 mg/mL) would be a clear advantage.

In the fourth installment of a series of seminal papers published on the preparation and properties of serum and plasma proteins, Cohn et al. (*J. Am. Chem. Soc.*, 1946, 68(3): 459-475) first described a methods for the alcohol fractionation of plasma proteins (method 6), which allows for the isolation of a fraction enriched in IgG from human plasma. Several years later, Oncley et al. (*J. Am. Chem. Soc.*, 1949, 71(2): 541-550) expanded upon the Cohn methods by publishing a method (method 9) that resulted in the isolation of a purer IgG preparation.

These methods, while laying the foundation for an entire industry of plasma derived blood factors, were unable to provide IgG preparations having sufficiently high concentrations for the treatment of several immune-related diseases, including Kawasaki syndrome, immune thrombocytopenic purpura, and primary immune deficiencies. As such, additional methodologies employing various techniques, such as ion exchange chromatography, were developed to provide higher purity and higher concentration IgG formulations. Hoppe et al. (*Munch Med Wochenschr* 1967 (34): 1749-1752) and Falksveden (Swedish Patent No. 348942) and Falksveden and Lundblad (*Methods of Plasma Protein Fractionation* 1980) were among the first to employ ion exchange chromatography for this purpose.

Various modern methods employ a precipitation step, such as caprylate precipitation (Lebing et al., *Vox Sang* 2003 (84): 193-201) and Cohn Fraction (I+)II+III ethanol precipitation (Tanaka et al., *Braz J Med Biol Res* 2000 (33)37-30) coupled to column chromatography. Most recently, Teschner et al. (*Vox Sang,* 2007 (92):42-55) have described a method for production of a 10% IVIG product in which cryo-precipitate is first removed from pooled plasma and then a modified Cohn-Oncley cold ethanol fractionation is performed, followed by S/D treatment of the intermediate, ion exchange chromatography, nanofiltration, and optionally ultrafiltration/diafiltration.

However, despite the improved purity, safety, and yield afforded by these IgG manufacturing methods, highly concentrated IgG preparations suitable for subcutaneous and/or intramuscular administration are still needed. The present invention fulfills these other needs and describes the manufacturing method of a stable, highly purified, virus inactivated, ready-to-use product with high concentration of IgG.

BRIEF SUMMARY OF THE INVENTION

In one aspect, the present invention provides an aqueous composition comprising more than about 180 grams of protein per liter of the composition, and at least 95% of the protein is IgG, such as human IgG. In some embodiments, the composition is produced by a process leading to a product suitable for subcutaneous and intravenous administration, and can be treated at elevated temperature in the final container to inactivate viruses regardless which concentration is adjusted between a concentration range of 10 to 22% of protein. In some cases, the protein concentration in the composition is at or about 20% (w/v). In other cases, the composition may further comprise about 0.1-0.3 M glycine. The composition of this invention may have varying pH, such as about 3-6, or about 4-6.

In another aspect, this invention provides a method for preparing a composition of concentrated IgG from plasma with the improvement comprising the steps of: (1) concentrating protein in a plasma preparation to at or about 5% (w/v) by ultrafiltration; and (2) further concentrating the protein in the preparation to at or about 20% (w/v) by diafiltration. At least 95% of the protein referred to in the composition is IgG, such as human IgG. In some embodiments, step (1) is performed using an ultrafiltration membrane with a nominal molecular weight cut off (NMWCO) of 100 kDa or less. In other embodiments, step (2) is performed against a diafiltration buffer of glycine with a pH of 4.2±0.1. The diafiltration buffer in some cases has 0.25 M glycine and a pH of 4.0. In some particular embodiments, the protein concentration after step (2) is higher than 20% (w/v) and is subsequently adjusted to at or about 20% (w/v) with a diafiltration buffer.

In another aspect, the invention provides a method for preparing a composition of concentrated IgG from plasma, comprising the steps of:
(1) separating liquid and precipitate from plasma by centrifugation;
(2) mixing pre-cooled ethanol with the liquid from (1) to form a mixture, which has an ethanol concentration of at or about 8% (v/v);
(3) separating liquid and precipitate from the mixture of (2) by centrifugation;
(4) adjusting pH and ethanol concentration of the liquid from (3) to at or about 7.0 and 20-25% (v/v), respectively, thereby forming a mixture;
(5) separating liquid and precipitate from the mixture of (4) by centrifugation,
(6) resuspending the precipitate of (5) with a buffer at a ratio of at or about 1 to 15 in weight to form a suspension;
(7) mixing silicon dioxide ($SiO_2$) with the suspension from (6) and obtaining a filtrate by filtration;
(8) mixing a detergent and cold alcohol with the filtrate of (7) and obtaining a precipitate by centrifugation;
(9) dissolving the precipitate in an aqueous solution comprising a solvent or detergent and maintaining the solution for at least 60 minutes;
(10) passing the solution after (9) through a cation exchange chromatography column and eluting proteins absorbed on the column in an eluate;
(11) passing the eluate from (10) through an anion exchange chromatography column to generate an effluent;
(12) passing the effluent through a nanofilter to generate a nanofiltrate;
(13) passing the nanofiltrate through an ultrafiltration membrane to generate an ultrafiltrate;
(14) diafiltrating the ultrafiltrate against a diafiltration buffer to generate a solution having a protein concentration of at or about 20% (w/v); and
(15) sterilizing the solution from (14) by filtering the solution through a filter of 0.2 µm or less, thereby obtaining a composition of concentrated IgG.

In some embodiments, step (2) is performed at a temperature of about −2 to 0° C.; or the mixture of step (2) is mixed for at least 15 minutes and then maintained for at least 2 hours at a temperature of about −2 to 0° C. In some embodiments, step (4) is mixed for at least 15 minutes and then maintained for at least 8 hours at a temperature of at or about −7° C. In some embodiments, the suspension of step (6) is stirred for about 40-160 minutes at a temperature of about 2° C. to 8° C. and a pH of at or about 5.0; or the silicon dioxide in step (7) is at a concentration of 40 g/kg of the suspension of step (6) and the mixing is performed at a temperature of about 2 to 8° C. for at least about 50 minutes. In some embodiments, step (8) is performed at a temperature of about −5 to −10° C. In some embodiments, the solution of step (9) comprises 1.0% (v/v) Triton X-100, 0.3% (v/v) Tween-80, and 0.3% (v/v) Tri-(n-butyl) phosphate (TNBP). In some embodiments, the solution of step (9) is maintained at a temperature of about 18 to 25° C. In some embodiments, the cation exchange chromatography column of step (10) is washed with a 10 mM acetate buffer of pH 5.5±0.1 and eluted with a buffer of 35 mM monobasic sodium phosphate, 10 mM Tris, pH 8.5±0.1, conductivity 5.0±0.2 mS/cm. In some embodiments, the eluate from step (10) is adjusted to a pH of 6.4±0.2 and conductivity of about 1.5 to 2.5 mS/cm prior to step (11). In some embodiments, the effluent of step (11) is passed through a filter of 0.2 µm or smaller pore size prior to step (12). In some embodiments, the ultrafiltrate of step (13) has a protein concentration of at or about 5±1% (w/v). In other embodiments, the ultrafiltration membrane of step (13) has a nominal molecular weight cut off (NMWCO) of 50 kDa or less. In some embodiments, the diafiltration buffer of step (14) is a 0.25 M glycine solution with a pH of 4.2±0.1. In other embodiments, the solution from step (14) has a protein concentration greater than 20% (w/v) and is subsequently adjusted to at or about 20.4±0.4% (w/v) with the diafiltration buffer. In some embodiments, steps (13) and (14) are performed at a temperature of about 2 to 8° C. In other embodiments, the preparation method further comprises a step of dispensing the sterilized solution of step (15) into containers under sterile conditions before the containers are sealed.

In other embodiments, the method described above may further comprise a step of storing the sealed containers at about 30 to 32° C. for about 21 to 22 days; or the method may further comprise a formulation step to render the 20% IgG product as stable as the 10% state of the art intravenous formulation.

In yet another aspect, this invention provides an aqueous composition that is produced by the preparation method described above and comprises at least 18% (w/v) immunoglobulin, for instance, at least 20% (w/v) immunoglobulin.

In a further aspect, the present invention provides a method for treating a patient suffering from an immunodeficiency, an autoimmune disease, or an acute infection, comprising administering to the patient an effective amount of the composition as described above.

DEFINITIONS

Figure 1A:
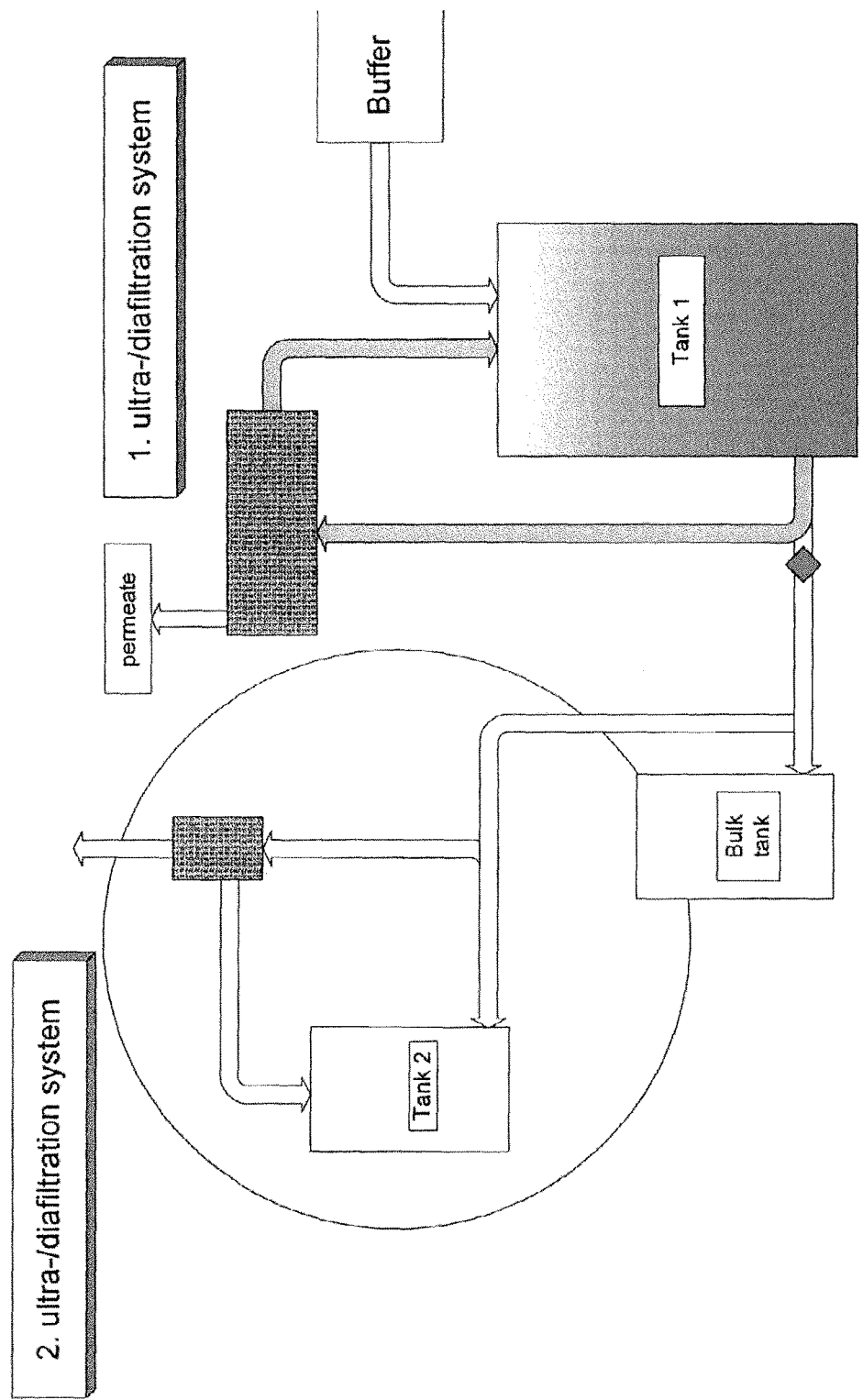
FIG. 1A, FIG. 1B, FIG. 1C, FIG. 1D and FIG. 1E are graphic illustrations of the new ultrafiltration/diafiltration system.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating colloids like proteins from small molecules like sugars and salts.

The term "diafiltration" is performed with the same membranes as ultrafiltration and is a tangential flow filtration. During diafiltration, buffer is introduced into the recycle tank while filtrate is removed from the unit operation. In processes where the product is in the retentate (for example IgG), diafiltration washes components out of the product pool into the filtrate, thereby exchanging buffers and reducing the concentration of undesirable species.

As used herein, the word "about" denotes an approximate range of plus or minus 10% from a specified value. For instance, the language "about 20%" encompasses a range of 18-22%.

The term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

In this application, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

The term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoate, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, the term "Intravenous IgG" or "IVIG" treatment refers generally to a therapeutic method of intravenously, subcutaneously, or intramuscularly administering a composition of IgG immunoglobulins to a patient for treating a number of conditions such as immune deficiencies, inflammatory diseases, and autoimmune diseases. The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titres for specific antigens (e.g., Rho D factor, pertussis toxin, tetanus toxin, botulism toxin, rabies, etc.). For ease of discussion, such subcutaneously or intramuscularly formulated IgG compositions are also included in the term "IVIG" in this application.

By "therapeutically effective amount or dose" or "sufficient/effective amount or dose," it is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins; the disclosures of which are incorporated by reference herein in their entireties for all purposes).

DETAILED DESCRIPTION OF THE INVENTION

As routinely practiced in modern medicine, sterilized preparations of concentrated immunoglobulins (especially IgGs) are used for treating medical conditions that fall into three main classes: immune deficiencies, inflammatory and autoimmune diseases, and acute infections. One commonly used IgG product, intravenous immunoglobulin or IVIG, is formulated for intravenous administration, for example, at a 10% concentration. Concentrated immunoglobulins may also be formulated for subcutaneous or intramuscular administration, for example at or about a 20% concentration.

In one aspect, the present invention relates to a new and improved method for producing highly purified and highly concentrated immunoglobulin compositions from pooled plasma. Compared to the previously used IgG purification and concentration methods, the inventors have incorporated ultrafiltration and formulation steps, which result in higher IgG concentration without significant IgG loss and maintain low pH in the final formulation. Typically, the products have a protein concentration of at least 18% weight/volume (w/v), of which vast majority (typically no less than 95%) is IgG, and a pH in the range of pH 3-6, which facilitates inactivation of pathogens such as viruses that may be present in the plasma. Due to their high IgG concentration and therefore reduced volume in administration, the products of this invention are suitable for subcutaneous and/or intramuscular administration. In some embodiments, the IgG products have a viscosity no greater than 18 mPascal-second and may therefore be suitable for intravenous administration as well. Due to the possibility to combine quality attributes for intravenous products with the required high concentration for subcutaneous and intramuscular products, simple dilution can also enable intravenous administration. A further advantage of the IgG composition of this invention is that they possess excellent stability during storage.

In certain aspects, the present invention provides methods for preparing a highly concentrated IgG preparation with a final protein concentrations of greater than about 17% and an IgG purity of at least about 95%. In certain embodiments, the preparation has an extended stability and is formulated for intravenous, subcutaneous, and/or intramuscular administration.

In another aspect, the present invention provides pharmaceutical compositions and formulations of IgG compositions prepared according to the improved manufacturing methodologies provided herein. In certain embodiments, these compositions and formulations provide improved properties as compared to other IVIG compositions currently on the market. For example, in certain embodiments, the compositions and formulations provided herein are stable for an extended period of time. In another embodiment, compositions and formulations provided herein have a higher IgG concentration as compared to other IVIG compositions currently on the market. In yet other embodiments, compositions and formulations provided herein have a higher IgG concentration and are stable for an extended period of time.

In yet another aspect, the present invention provides method for treating immune deficiencies, inflammatory and autoimmune diseases, and acute infections comprising the administration of an IgG composition prepared using the improved methods provided herein.

1. Producing a Concentrated, Purified IgG Preparation

IVIG compositions comprising whole antibodies have been described for the treatment of certain autoimmune conditions. (See, e.g., U.S. Patent Publication US 2002/0114802, US 2003/0099635, and US 2002/0098182.) The IVIG compositions disclosed in these references include polyclonal antibodies.

Generally, immunoglobulin preparations according to the present invention can be prepared from any suitable starting materials, for example, recovered plasma or source plasma. In a typical example, blood or plasma is collected from healthy donors. Usually, the blood is collected from the same species of animal as the subject to which the immunoglobulin preparation will be administered (typically referred to as "homologous" immunoglobulins). The immunoglobulins are isolated from the blood by suitable procedures, such as, for example, precipitation (alcohol fractionation or polyethylene glycol fractionation), chromatographic methods (ion exchange chromatography, affinity chromatography, immunoaffinity chromatography) ultracentrifugation, and electrophoretic preparation, and the like. (See, e.g., Cohn et al., *J. Am. Chem. Soc.* 68:459-75 (1946); Oncley et al., *J. Am. Chem. Soc.* 71:541-50 (1949); Barundern et al., *Vox Sang.* 7:157-74 (1962); Koblet et al., *Vox Sang.* 13:93-102 (1967); U.S. Pat. Nos. 5,122,373 and 5,177,194; the disclosures of which are incorporated by reference herein in their entireties for all purposes).

Unlike the methods described above, in one aspect the present invention provides methods of preparing concentrated IgG compositions that utilize a cryo-poor starting material. Generally, the methods provided herein utilize both modified Cohn-Oncley alcohol fractionation steps and ion exchange chromatography to provide superior IgG yields, while maintaining the same, if not improved, quality as found in currently available commercial IVIG preparations.

In many cases, immunoglobulin is prepared from gamma globulin-containing products produced by the alcohol fractionation and/or ion exchange and affinity chromatography methods well known to those skilled in the art. Purified Cohn Fraction II is commonly used. The starting Cohn Fraction II paste is typically at or about 95 percent IgG and is comprised of the four IgG subtypes. The different subtypes are present in Fraction II in approximately the same ratio as they are found in the pooled human plasma from which they are obtained. The Fraction II is further purified before formulation into an administrable product. For example, the Fraction II paste can be dissolved in a cold purified aqueous alcohol solution and impurities removed via precipitation and filtration. Following the final filtration, the immunoglobulin suspension can be dialyzed or diafiltered (e.g., using ultrafiltration membranes having a nominal molecular weight limit of less than or equal to 100,000 daltons) to remove the alcohol. The solution can be concentrated or diluted to obtain the desired protein concentration and can be further purified by techniques well known to those skilled in the art.

Preparative steps can be used to enrich a particular isotype or subtype of immunoglobulin. For example, protein A, protein G or protein H sepharose chromatography can be used to enrich a mixture of immunoglobulins for IgG, or for specific IgG subtypes. (See generally Harlow and Lane, *Using Antibodies*, Cold Spring Harbor Laboratory Press (1999); Harlow and Lane, *Antibodies, A Laboratory Manual*, Cold Spring Harbor Laboratory Press (1988); U.S. Pat. No. 5,180,810.)

As will be described in detail below, the high concentration IgG products of this invention are produced by a process having many of the same or similar steps as in the process of producing IVIG. The additional steps of ultrafiltration/diafiltration using open channel membranes with a specifically designed post-wash and formulation near the end the production process render the resulting IgG compositions about twice as high in protein concentration (200 mg/mL) compared to state of the art IVIGs (e.g., GAMMAGARD® LIQUID) without affecting yield and storage stability. With most of the commercial available ultrafiltration membranes a concentration of 200 mg/mL IgG cannot be reached without major protein losses. These membranes will be blocked early and therefore adequate post-wash is difficult to achieve. Therefore open channel membrane configurations have to be used. Even with open channel membranes, a specifically designed post-wash procedure has to be used to obtain the required concentration without significant protein loss (less than 2% loss). Even more surprising is the fact that the higher protein concentration of 200 mg/mL does not effect the virus inactivation capacity of the low pH storage step. The general process of producing the high concentration IgG composition includes the following steps:

A. Separation of Cryoprecipitates

The purification process typically starts with thawing previously frozen pooled plasma, already checked for safety and quality considerations. Thawing is typically carried out at a temperature no higher than 6° C. Centrifugation or filtration is then performed in the cold to separate solid and liquid upon plasma being thawed, usually at the same low temperature as thawing. The liquid portion (also referred to as "cryo-poor plasma," after cold-insoluble proteins removed by centrifugation or filtration from fresh thawed plasma) is then processed in the next step. Various additional steps can be taken at this juncture for the isolation of factor eight inhibitor bypass activity (FEIBA), Factor IX-complex, Factor VII-concentrate, or Antithrombin III-complex, which are described in detail in Example 1.

B. Obtain Supernatant of Fractionation I

In this step, cyro-poor plasma is typically cooled to at or about 0±1° C., and its pH is adjusted to at or about 7.0. In certain embodiments, the pH is adjusted to between about 7.0 and about 7.5, preferably between at or about 7.1 and at or about 7.3, most preferably at or about 7.2. In one embodiment, the pH is adjusted to at or about 7.0. In another embodiment, the pH is adjusted to at or about 7.1. In another embodiment, the pH is adjusted to at or about 7.2. In another embodiment, the pH is adjusted to at or about 7.3. In another embodiment, the pH is adjusted to at or about 7.4. In another embodiment, the pH is adjusted to at or about 7.5. Pre-cooled ethanol is then added while the plasma is being stirred to a target concentration of ethanol at 8% v/v. At the same time the temperature is further lowered to between about −4 and about 0° C., preferably about −2° C., to precipitate contaminants such as $\alpha_2$-macroglobulin, $\beta_{1A}$- and $\beta_{1C}$-globulin, fibrinogen, and Factor VIII. Typically, the precipitation event will include a hold time of at least about 1 hour, although shorter or longer hold times may also be employed. Subsequently, the supernatant (Supernatant I), ideally containing the entirety of the IgG content present in the cryo-poor plasma, is then collected by centrifugation, filtration, or another suitable method.

C. Precipitate of Fractionation II+III

To further enrich the IgG content and purity of the fractionation, Supernatant I is subjected to a second precipitation step. Generally, the pH of the solution is adjusted to a pH of between about 6.8 and about 7.2, preferably at or about 7.0. Alcohol, preferably ethanol, is then added to the solution while being stirred to a final concentration of between about 20% and about 25% (v/v). In one embodiment, the final concentration of alcohol is at or about 20%. In another embodiment, the final alcohol concentration is at or about 21%. In another embodiment, the final alcohol concentration is at or about 22%. In another embodiment, the final alcohol concentration is at or about 23%. In another embodiment, the final alcohol concentration is at or about 24%. In another embodiment, the final alcohol concentration is at or about 25%. The liquid portion, also referred to as Fraction II+III supernatant, can be further processed to extract Factor V. The precipitate from this step is processed further in the next step. In one embodiment, steps B and C can also be performed together.

D. Extraction from Fractionations II and III Precipitate

A cold extraction buffer is used to resuspend the Fraction II+III precipitate at a typical ratio of 1 part of precipitate in 15 parts of extraction buffer. An exemplary extraction buffer contains 5 mM monobasic sodium phosphate and 5 mM acetate, and has a pH at or about 4.5±0.2 and conductivity of at or about 0.7 to 0.9 mS/cm. In one embodiment, the conductivity of the extraction buffer is at or about 0.7 mS/cm. In another embodiment, the conductivity of the extraction buffer is at or about 0.8 mS/cm. In yet another embodiment, the conductivity of the extraction buffer is at or about 0.9 mS/cm. The extraction process is performed at a temperature of at or about 2 to 8° C.

Other suitable re-suspension ratios may be used, for example from about 1:8 to about 1:30, or from about 1:10 to about 1:20, or from about 1:12 to about 1:18, or from about 1:13 to about 1:17, or from about 1:14 to about 1:16. In certain embodiments, the re-suspension ratio may be at or about 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the II+III precipitate will generally have a pH between about 4.0 and about 5.5. In certain embodiments, the solution will have a pH between about 4.0 and about 5.0. In another embodiment, the solution will have a pH between about 4.5 and about 5.0. In other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In one embodiment, the pH of the extraction buffer will be at or about 4.5. In another embodiment, the pH of the extraction buffer will be at or about 4.6. In another embodiment, the pH of the extraction buffer will be at or about 4.7. In another embodiment, the pH of the extraction buffer will be at or about 4.8. In another embodiment, the pH of the extraction buffer will be at or about 4.9. In another embodiment, the pH of the extraction buffer will be at or about 5.0.

The extraction buffer will preferably have a conductivity of from about 0.5 $mS \cdot cm^{-1}$ to about 2.0 $mS \cdot cm^{-1}$. For example, in certain embodiments, the conductivity of the extraction buffer will be at or about 0.5 $mS \cdot cm^{-1}$, or at or about 0.6, 0.7, 0.8, 0.9, 1.0, 1.1, 1.2, 1.3, 1.4, 1.5, 1.6, 1.7, 1.8, 1.9, or about 2.0 $mS \cdot cm^{-1}$. One of ordinary skill in the art will know how to generate extraction buffers having an appropriate conductivity.

E. Fumed Silica Treatment and Filtration

In some embodiment, fumed silica (e.g., Aerosil 380 or equivalent) is added to the suspension from the last step to a concentration of at or about 40 g/kg of suspension, or equivalent to 1.8 g/liter of cryo-poor plasma. Mixing takes place at about 2 to 8° C. for at least 50 to 70 minutes. In some cases, filter aid (e.g., Hyflo-Supper-Cel from World Minerals, used at a concentration of at or about 0.5 kg/kg of suspension) is added to facilitate the subsequent step of liquid/solid separation by filtration. The extraction buffer is used for post-washing of the filter press. The filtration process is maintained at a temperature of about 2 to 8° C.

F. Fractionation of Precipitate G

Filtrate from the last step is then mixed with polysorbate-80 to a concentration of at or about 0.2% w/v with stirring for at least 30 minutes at a temperature of about 2° C. to 8° C. Sodium citrate dehydrate is then mixed into the solution at or about 8 g/liter for another 30 minutes of stirring at a temperature of about 2° C. to 8° C. The solution's pH is then adjusted to at or about 7.0±0.1. In certain embodiments, the pH is adjusted with either sodium hydroxide or acetic acid. Cold alcohol is then added to the solution to a concentration of at or about 25% v/v, and a precipitation step similar to Cohn II is performed.

G. Suspension of Precipitate G

The precipitate from the last step is dissolved and filtered with a depth filter of a nominal pore size of 0.2 μm (e.g., Cuno VR06 filter or equivalent) to obtain a clear filtrate. In another embodiment, the precipitate is dissolved and then centrifuged to recover a clarified supernatant.

H. Solvent and Detergent Treatment

The filtrate from the last step is used for the solvent-/detergent treatment. A typical solvent/detergent treatment mixture comprises 1.0% (v/v) Triton X-100, 0.3% (v/v) Tween-80, and 0.3% (v/v) TNBP, and the mixture is typically held at a temperature of about 18° C. to 25° C. for at least 60 minutes. Methods for the detergent treatment of plasma derived fractions are well known in the art. Generally, any standard non-ionic detergent treatment may be used in conjunction with the methods provided herein.

I. Cation Exchange Chromatography

In order to further purify and concentrate IgG from the S/D treated PptG filtrate, cation exchange and/or anion exchange chromatography can be employed. Methods for purifying and concentrating IgG using ion exchange chromatography are well known in the art. For example, U.S. Pat. No. 5,886,154 describes a method in which a Fraction II+III precipitate is extracted at low pH (between about 3.8 and 4.5), followed by precipitation of IgG using caprylic acid, and finally implementation of two anion exchange chromatography steps. U.S. Pat. No. 6,069,236 describes a chromatographic IgG purification scheme that does not rely on alcohol precipitation at all. PCT Publication No. WO 2005/073252 describes an IgG purification method involving the extraction of a Fraction II+III precipitate, caprylic acid treatment, PEG treatment, and a single anion exchange chromatography step. U.S. Pat. No. 7,186,410 describes an IgG purification method involving the extraction of either a Fraction I+II+III or a Fraction II precipitate followed by a single anion exchange step performed at an alkaline pH. U.S. Pat. No. 7,553,938 describes a method involving the extraction of either a Fraction I+II+III or a Fraction II+III precipitate, caprylate treatment, and either one or two anion exchange chromatography steps. U.S. Pat. No. 6,093,324 describes a purification method comprising the use of a macroporous anion exchange resin operated at a pH between about 6.0 and about 6.6. U.S. Pat. No. 6,835,379 describes a purification method that relies on cation exchange chromatography in the absence of alcohol fractionation.

In one embodiment, the solvent/detergent containing protein solution from the last step is then passed through a cation exchange column to remove the solvent and detergent. After washing out of SD reagents, the absorbed proteins are then eluted with high pH elution buffer. In one embodiment, the elution buffer will have a pH of between about 7.5 and about 9.5. In another embodiment, the elution buffer will have a pH of between about 8.0 and about 9.0. In a preferred embodiment, the elution buffer will have a pH of at or about 8.5±0.1.

J. Anion Exchange Chromatography

The eluate from the last step is adjusted to pH 6 and diluted to the appropriate conductivity for the following equilibrated anion exchange column. The column flow-through during loading and washing is collected for further processing.

K. Nanofiltration

In order to further reduce the viral load of the IgG composition provided herein, the anion exchange column effluent may be nanofiltered using a suitable nanofiltration device. In certain embodiments, the nanofiltration device will have a mean pore size of between about 15 nm and about 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of at or about 15 nm, 19 nm, 35 nm, or 72 nm. In a preferred embodiment, the nanofilter will have a mean pore size of at or about 35 nm, such as an Asahi PLANOVA 35N filter or equivalent thereof.

L. Ultrafiltration and Diafiltration

Subsequent to nanofiltration, the filtrate is further concentrated to a protein concentration of 5±1% w/v by ultrafiltration. In some examples, the ultrafiltration is carried out in a cassette with an open channel screen and the ultrafiltration membrane has a nominal molecular weight cut off (NMWCO) of 50 kDa or less.

In one embodiment, the nanofiltrate may be concentrated by ultrafiltration to a protein concentration of between about 2% and about 10% (w/v). In certain embodiments, the ultrafiltration is carried out in a cassette with an open channel screen and the ultrafiltration membrane has a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa.

Upon completion of the ultrafiltration step, the concentrate may further be concentrated via diafiltration against a solution suitable for intravenous or intramuscular administration. In certain embodiments, the diafiltration solution may comprise a stabilizing and/or buffering agent. In a preferred embodiment, the stabilizing and buffering agent is glycine at an appropriate concentration, for example between about 0.20 M and about 0.30M, or between about 0.22M and about 0.28M, or between about 0.24M and about 0.26 mM, or at a concentration of at or about 2.0, 2.1, 2.2, 2.3, 2.4, 2.5, 2.6, 2.7, 2.8, 2.9, or 3.0. In a preferred embodiment, the diafiltration buffer contains at or about 0.25 M glycine.

In a preferred embodiment, upon completion of the ultrafiltration step, the concentrate is diafiltered against a 0.25 M glycine solution with a low pH. Typically, the minimum exchange volume is 6 times of the original concentrate volume, and the solution is concentrated to a protein concentration of more than 20% w/v. At the end of the diafiltration and concentration process, the pH of the solution is typically between 4.4 to 4.9.

Typically, the minimum exchange volume is at least about 3 times the original concentrate volume or at least about 4, 5, 6, 7, 8, 9, or more times the original concentrate volume. The IgG solution may be concentrated to a final protein concentration of between about 5% and about 22% (w/v), or between about 10% and about 22% (w/v), or between about 15% and about 22% (w/v), or between about 18% and about 22% (w/v), or between about 20% and about 22%, or to a final concentration of at or about 5%, or 6%, 7%, 8%, 9%, 10%, 11%, 12%, 13%, 14%, 15%, 16%, 17%, 18%, 19%, 20%, 21%, 22%, or higher. In a preferred embodiment, the IgG solution will be concentrated to final protein concentration of at or between about 20% and at or between 22%. Typically, at the end of the concentration process, the pH of the solution will be between about 4.6 to 5.1.

FIGS. 1A-1E illustrate an exemplary method for ultrafiltration/diafiltration according to an embodiment of the disclosure. First, a sample (e.g., a nanofiltrate) is concentrated to a first concentration to form a first concentrate. The first concentrate is diafiltered against a diafiltration buffer to form a diafiltrate. The diafiltrate is then concentrated to a protein value of greater than 22% to form a second concentrate. These steps are performed in a first ultra-/diafiltration system including a first batch tank and a first membrane, as shown in FIG. 1A. In some embodiments, the first batch tank is designed to hold small volumes, ideally by a conical bottom.

Figure 1B:
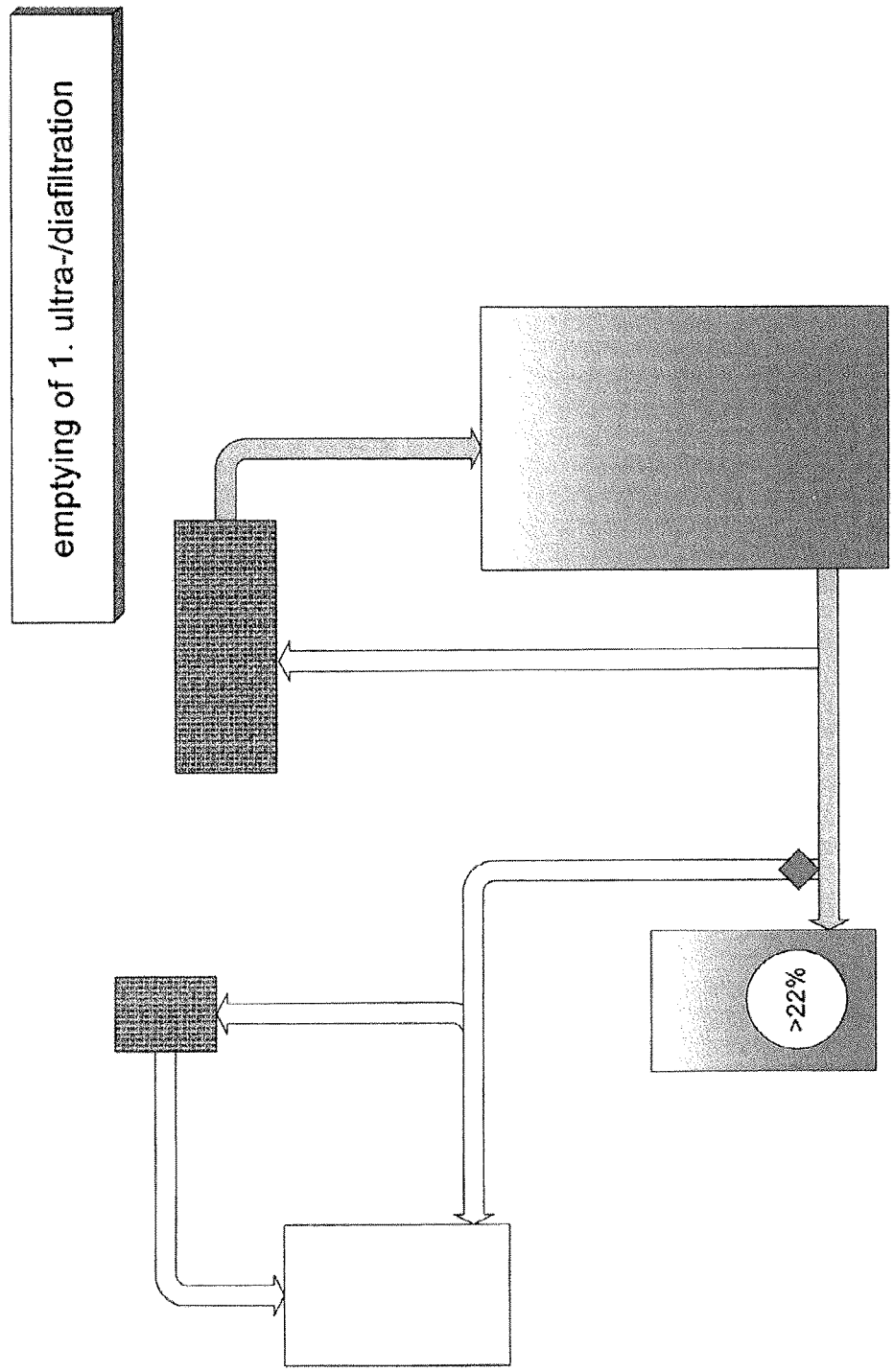
Figure 1C:
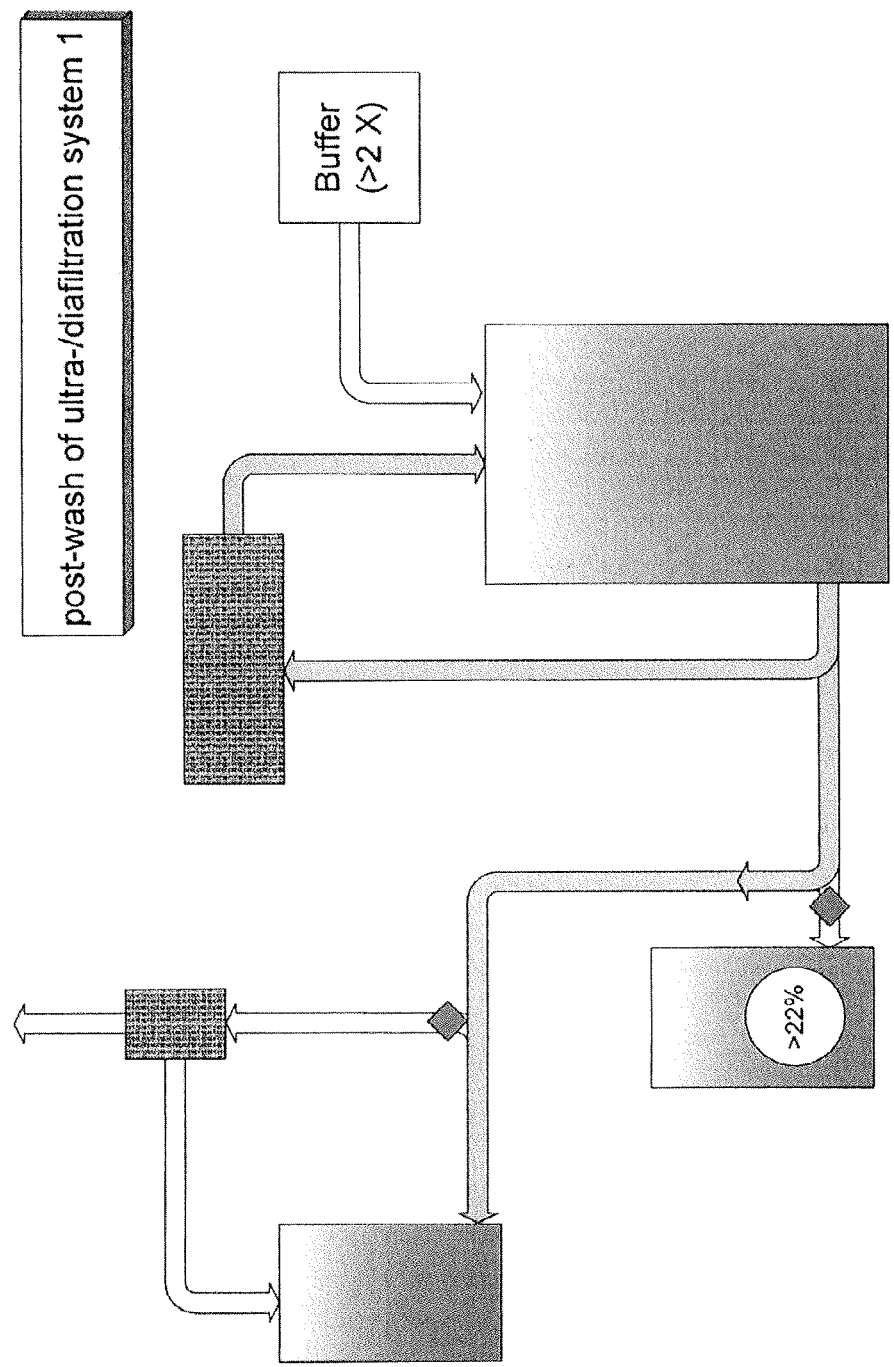

The second concentrate is then emptied from the first ultra-/diafiltration system, e.g., into a bulk tank, as shown in FIG. 1B. The first ultra-/diafiltration system is then post-washed by re-circulation of a post wash buffer through the first ultra-/diafiltration system. The post-wash is transferred to a second, smaller, ultra-/diafiltration system that includes a second batch tank and a second membrane, as shown in FIG. 1C. The second membrane is the same type of membrane as used in the first ultra-/diafiltration system.

Figure 1D:
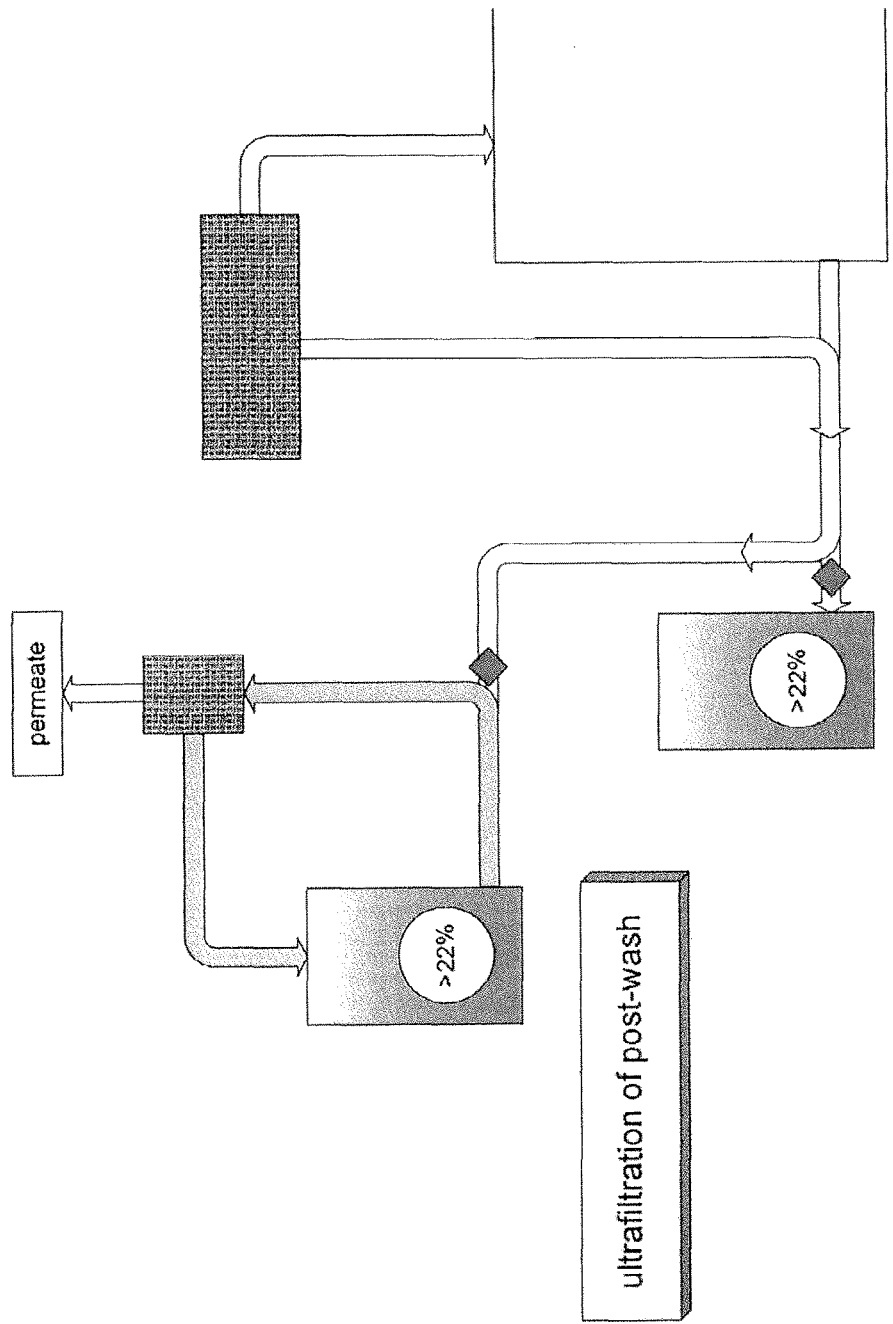
Figure 1E:
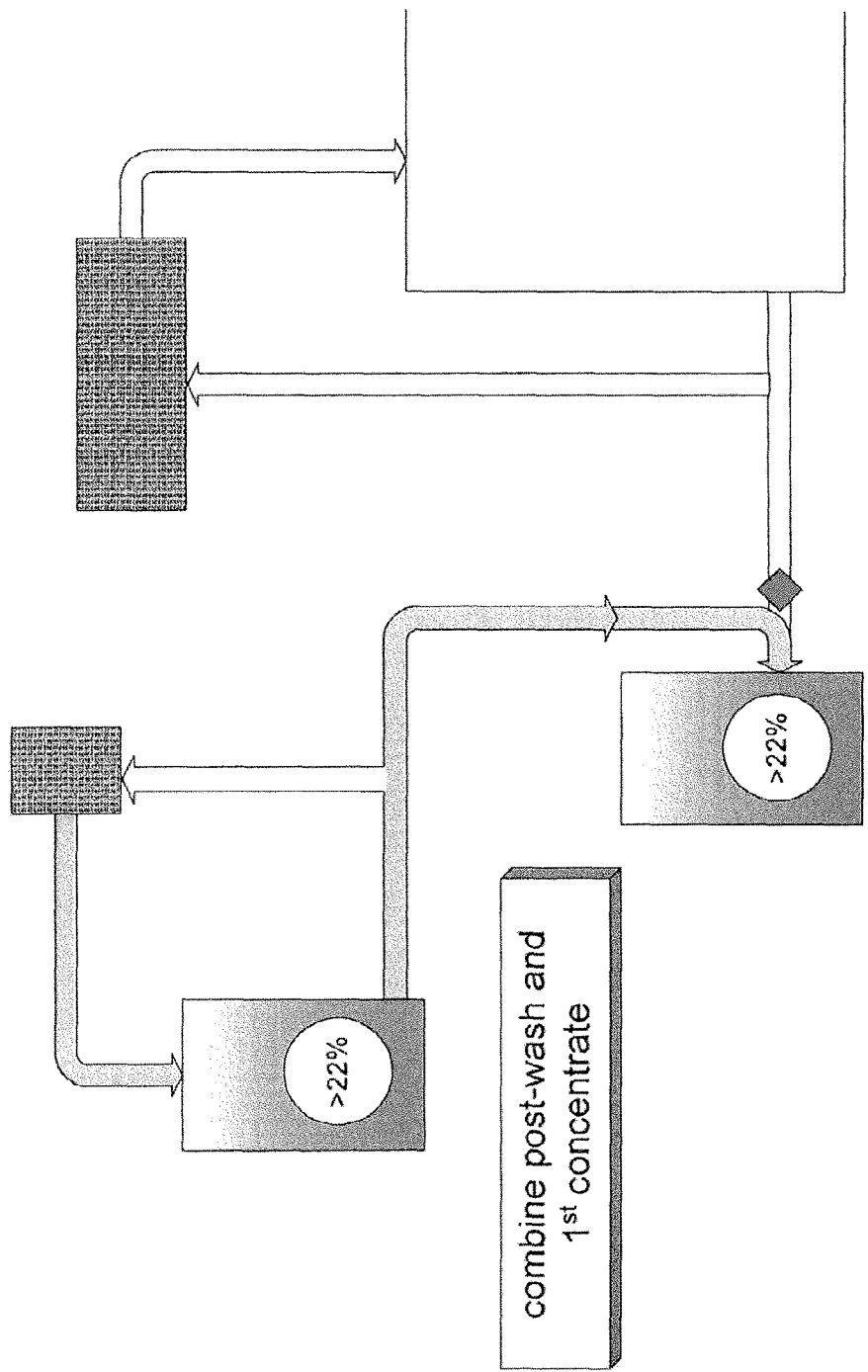

The post-wash is then concentrated in the second ultra-/diafiltration system to form a second concentrate, as shown in FIG. 1D. The second concentrate is then combined with the first concentrate, e.g., in the bulk tank, as shown in FIG. 1E. The second ultra-/diafiltration system can be post-washed, and the post-wash used to adjust the final protein concentration of the combined bulk solution, e.g., to 20.4%±0.4 w/v, not shown. The final bulk may be sterile filtered and filled into a final container.

M. Formulation

Upon completion of the diafiltration step, the protein concentration of the solution is adjusted to with the diafiltration buffer to a final concentration of between about 5% and about 20% (w/v), or between about 10% and about 20% (w/v), or between about 15% and about 20% (w/v), or between about 18% and about 20% (w/v), or to a final concentration of about 5%, or 6%, 7%, 8%, 9%, 10%, 11%, 12%, 13%, 14%, 15%, 16%, 17%, 18%, 19%, or 20%. In a preferred embodiment, the final protein concentration of the solution is at or between about 19%, and at or about 21%. In a preferred embodiment, upon completion of diafiltration, the protein concentration of the solution is adjusted to just over 20% w/v, e.g., at or about 20.4±04% w/v, with the diafiltration buffer.

N. Further Sterilization

The formulated bulk solution is further sterilized by first filtering through a membrane filter with an absolute pore size of 0.2 micron or less. Then the solution is aseptically dispensed into final containers for proper sealing, with samples taken for testing. The final step is storing the sealed containers at 30 to 32° C. for an extended time period, e.g., 21 to 22 days.

II. Concentrated IgG Compositions

In one aspect, the present invention relates to aqueous IgG compositions prepared by the methods provided herein. Generally, the IgG compositions prepared by the novel methods described herein will have high IgG content and purity. For example, IgG compositions provided herein may have a protein concentration of at least about 15% (w/v) and an IgG content of greater than 90% purity. These high purity IgG compositions are suitable for therapeutic administration, e.g., for subcutaneous and/or intramuscular administration. In one embodiment, the IgG compositions provided herein are suitable for intravenous administration, for example by diluting prior to administration. In one embodiment, the concentration of IgG is at or about 20% and is used for subcutaneous or intramuscular administration.

In one embodiment, the present invention provides an aqueous IgG composition prepared by a method comprising the steps of:

(1) separating liquid and precipitate from plasma by centrifugation;
(2) mixing pre-cooled ethanol with the liquid from (1) to form a mixture, which has an ethanol concentration of at or about 8% (v/v);
(3) separating liquid and precipitate from the mixture of (2) by centrifugation;
(4) adjusting pH and ethanol concentration of the liquid from (3) to at or about 7.0 and 20-25% (v/v), respectively, thereby forming a mixture;
(5) separating liquid and precipitate from the mixture of (4) by centrifugation;
(6) resuspending the precipitate of (5) with a buffer at a ratio of about 1 to 15 in weight to form a suspension;
(7) mixing silicon dioxide ($SiO_2$) with the suspension from (6) and obtaining a filtrate by filtration;
(8) mixing a detergent and cold alcohol with the filtrate of (7) and obtaining a precipitate by centrifugation;
(9) dissolving the precipitate in an aqueous solution comprising a solvent or detergent and maintaining the solution for at least 60 minutes;
(10) passing the solution after (9) through a cation exchange chromatography column and eluting proteins absorbed on the column in an eluate;
(11) passing the eluate from (10) through an anion exchange chromatography column to generate an effluent;
(12) passing the effluent through a nanofilter to generate a nanofiltrate;
(13) passing the nanofiltrate through an ultrafiltration membrane to generate an ultrafiltrate;
(14) diafiltrating the ultrafiltrate against a diafiltration buffer to generate a solution having a protein concentration of at or about 20% (w/v); and
(15) sterilizing the solution from (14) by filtering the solution through a filter of 0.2 μm or less, thereby obtaining a composition of concentrated IgG.

In one embodiment, the present invention provides aqueous IgG compositions comprising a protein concentration of between about 150 g/L and about 250 g/L. In certain embodiments, the protein concentration of the IgG composition is between about 175 g/L and about 225 g/L, or between about 200 g/L and about 225 g/L, or any suitable concentration within these ranges, for example at or about, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, the aqueous IgG composition comprises a protein concentration of at or about 200 g/L. In a particularly preferred embodiment, the aqueous IgG composition comprises a protein concentration of at or about 204 g/L.

The methods provided herein allow for the preparation of IgG compositions having very high levels of purity. For example, in one embodiment, at least about 95% of the total protein in a composition provided herein will be IgG. In other embodiments, at least about 96% of the protein is IgG, or at least about 97%, 98%, 99%, 99.5%, or more of the total protein of the composition will be IgG.

Similarly, the methods provided herein allow for the preparation of IgG compositions which containing extremely low levels of contaminating agents. For example, in certain embodiments, IgG compositions are provided that contain less than about 100 mg/L IgA. In other embodiments, the IgG composition will contain less than about 50 mg/L IgA, preferably less than about 35 mg/L IgA, most preferably less than about 20 mg/L IgA.

III. Pharmaceutical Compositions

In another aspect, the present invention provides pharmaceutical compositions and formulations comprising purified IgG prepared by the methods provided herein. Generally, the IgG pharmaceutical compositions and formulations prepared by the novel methods described herein will have high IgG content and purity. For example, IgG pharmaceutical compositions and formulations provided herein may have a protein concentration of at least about 15% (w/v) and an IgG content of greater than 90% purity. These high purity IgG compositions are suitable for therapeutic administration, e.g., for subcutaneous and/or intramuscular administration. In one embodiment, the IgG compositions provided herein are suitable for intravenous administration, for example by diluting prior to administration. In one embodiment, the concentration of IgG is at or about 20% and is used for subcutaneous or intramuscular administration.

In one embodiment, the pharmaceutical compositions provided herein are prepared by formulating an aqueous IgG composition isolated using a method provided herein. Generally, the formulated composition will have been subjected to at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43): 1023-1028, both of which are herein expressly incorporated by reference in their entirety for all purposes), nanofiltration (Hamamoto et al., *Vox Sang* 1989 (56)230-236 and Yuasa et al., *J Gen Virol*. 1991 (72 (pt 8)):2021-2024, both of which are herein expressly incorporated by reference in their entirety for all purposes), and low pH incubation at high temperatures (Kempf et al., *Transfusion* 1991 (31)423-427 and Louie et al., *Biologicals* 1994 (22):13-19).

In certain embodiments, pharmaceutical formulations are provided having an IgG content of between about 175 g/L IgG and about 225 g/L IgG. Generally, these IVIG formulations are prepared by isolating an IgG composition from plasma using a method described herein, concentrating the composition, and formulating the concentrated composition in a solution suitable for intravenous administration. The IgG compositions may be concentrated using any suitable method known to one of skill in the art. In one embodiment, the composition is concentrated by ultrafiltration/diafiltration. In some embodiments, the ultrafiltration device used to concentrate the composition will employ an ultrafiltration membrane having a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa. Buffer exchange may be achieved using any suitable technique known to one of skill in the art. In a specific embodiment, buffer exchange is achieved by diafiltration.

In a specific embodiment, a pharmaceutical composition of IgG is provided, wherein the IgG composition was purified from plasma using a method comprising the steps of
  (1) separating liquid and precipitate from plasma by centrifugation;
  (2) mixing pre-cooled ethanol with the liquid from (1) to form a mixture, which has an ethanol concentration of at or about 8% (v/v);
  (3) separating liquid and precipitate from the mixture of (2) by centrifugation;
  (4) adjusting pH and ethanol concentration of the liquid from (3) to at or about 7.0 and 20-25% (v/v), respectively, thereby forming a mixture;
  (5) separating liquid and precipitate from the mixture of (4) by centrifugation;
  (6) resuspending the precipitate of (5) with a buffer at a ratio of about 1 to 15 in weight to form a suspension;
  (7) mixing silicon dioxide (SiO2) with the suspension from (6) and obtaining a filtrate by filtration;
  (8) mixing a detergent and cold alcohol with the filtrate of (7) and obtaining a precipitate by centrifugation;
  (9) dissolving the precipitate in an aqueous solution comprising a solvent or detergent and maintaining the solution for at least 60 minutes;
  (10) passing the solution after (9) through a cation exchange chromatography column and eluting proteins absorbed on the column in an eluate;
  (11) passing the eluate from (10) through an anion exchange chromatography column to generate an effluent;
  (12) passing the effluent through a nanofilter to generate a nanofiltrate;
  (13) passing the nanofiltrate through an ultrafiltration membrane to generate an ultrafiltrate;
  (14) diafiltrating the ultrafiltrate against a diafiltration buffer to generate a solution having a protein concentration of about 20% (w/v); and
  (15) sterilizing the solution from (14) by filtering the solution through a filter of 0.2 μm or less, thereby obtaining a composition of concentrated IgG.

In one embodiment, the present invention provides pharmaceutical IgG compositions comprising a protein concentration of between about 150 g/L and about 250 g/L. In certain embodiments, the protein concentration of the IgG composition is between about 175 g/L and about 225 g/L, or between about 200 g/L and about 225 g/L, or any suitable concentration within these ranges, for example at or about, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, the aqueous IgG composition comprises a protein concentration of at or about 200 g/L. In a particularly preferred embodiment, the aqueous IgG composition comprises a protein concentration of at or about 204 g/L.

The methods provided herein allow for the preparation of IgG pharmaceutical compositions having very high levels of purity. For example, in one embodiment, at least about 95% of the total protein in a composition provided herein will be IgG. In other embodiments, at least about 96% of the protein is IgG, or at least about 97%, 98%, 99%, 99.5%, or more of the total protein of the composition will be IgG.

Similarly, the methods provided herein allow for the preparation of IgG pharmaceutical compositions which containing extremely low levels of contaminating agents. For example, in certain embodiments, IgG compositions are provided that contain less than about 100 mg/L IgA. In other embodiments, the IgG composition will contain less than about 50 mg/L IgA, preferably less than about 35 mg/L IgA, most preferably less than about 20 mg/L IgA.

The pharmaceutical compositions provided herein will typically comprise one or more buffering agents or pH stabilizing agents suitable for intravenous administration. Non-limiting examples of buffering agents suitable for formulating an IgG composition provided herein include glycine, citrate, phosphate, acetate, glutamate, tartrate, benzoate, lactate, histidine or other amino acids, gluconate, malate, succinate, formate, propionate, carbonate, or any combination thereof adjusted to an appropriate pH. Generally, the buffering agent will be sufficient to maintain a suitable pH in the formulation for an extended period of time. In a preferred embodiment, the buffering agent is glycine.

In some embodiments, the concentration of buffering agent in the formulation will be between about 100 mM and about 400 mM, preferably between about 150 mM and about 350 mM, more preferably between about 150 mM and about 300 mM, most preferably between about 175 mM and about 225 mM. In a particularly preferred embodiment, the concentrated IgG composition will comprise between about 150 mM and about 250 mM glycine, most preferably about 200 mM glycine. In another preferred embodiment, the concentrated IgG composition will contain at or about 250 mM glycine.

In certain embodiments, the pH of the formulation will be between about 4.1 and about 5.6, preferably between about 4.4 and about 5.3, most preferably between about 4.6 and about 5.1. In particular embodiments, the pH of the formulation may be about 4.1, 4.2, 4.3, 4.4, 4.5, 4.6, 4.7, 4.8, 4.9, 5.0, 5.1, 5.2, 5.3, 5.4, 5.5, or 5.6.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

Typically, the formulations provided herein will have osmolarities that are comparable to physiologic osmolarity, about 285 to 295 mOsmol/kg (Lacy et al., *Drug Information Handbook—Lexi-Comp* 1999:1254. In certain embodiments, the osmolarity of the formulation will be between about 200 mOsmol/kg and about 350 mOsmol/kg, preferably between about 240 and about 300 mOsmol/kg. In particular embodiments, the osmolarity of the formulation will be about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg.

The IgG formulations provided herein are generally stable in liquid form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, or 24 months at room temperature. The formulation will also generally be stable for at least about 18 months under refrigerated conditions (typically between about 2° C. and about 8° C.), or for at least about 21, 24, 27, 30, 33, 36, 39, 42, or 45 months under refrigerated conditions.

IV. Administration of the IgG Preparation

As routinely practiced in the modern medicine, sterilized preparations of concentrated immunoglobulins (especially IgGs) are used for treating medical conditions that fall into these three main classes: immune deficiencies, inflammatory and autoimmune diseases, and acute infections. These IgG preparations may also be useful for treating multiple sclerosis (especially relapsing-remitting multiple sclerosis or RRMS), Alzheimer's disease, and Parkinson's disease. The purified IgG preparation of this invention is suitable for these purposes, as well as other clinically accepted uses of IgG preparations.

The FDA has approved the use of IVIG to treat various indications, including allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), and kidney transplant with a high antibody recipient or with an ABO incompatible donor. In certain embodiments, the IVIG compositions provided herein are useful for the treatment or management of these diseases and conditions.

Furthermore, off-label uses for IVIG are commonly provided to patients for the treatment or management of various indications, for example, chronic fatigue syndrome, *clostridium difficile* colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, and hypogammaglobulinemia. In certain embodiments, the IVIG compositions provided herein are useful for the treatment or management of these diseases and conditions.

Finally, experimental use of IVIG for the treatment or management of diseases including primary immune deficiency, RRMS, Alzheimer's disease, and Parkinson's disease has been proposed (U.S. Patent Application Publication No. U.S. 2009/0148463, which is herein incorporated by reference in its entirety for all purposes). In certain embodiments, the IVIG compositions provided herein are useful for the treatment or management of primary immune deficiency, RRMS, Alzheimer's disease, or Parkinson's disease. In certain embodiments comprising daily administration, an effective amount to be administered to the subject can be determined by a physician with consideration of individual differences in age, weight, disease severity, route of administration (e.g., intravenous v. subcutaneous) and response to the therapy. In certain embodiments, an immunoglobulin preparation of this invention can be administered to a subject at about 5 mg/kilogram to about 2000 mg/kilogram each day. In additional embodiments, the immunoglobulin preparation can be administered in amounts of at least about 10 mg/kilogram, at last 15 mg/kilogram, at least 20 mg/kilogram, at least 25 mg/kilogram, at least 30 mg/kilogram, or at least 50 mg/kilogram. In additional embodiments, the immunoglobulin preparation can be administered to a subject at doses up to about 100 mg/kilogram, to about 150 mg/kilogram, to about 200 mg/kilogram, to about 250 mg/kilogram, to about 300 mg/kilogram, to about 400 mg/kilogram each day. In other embodiments, the doses of the immunoglobulin preparation can be greater or less. Further, the immunoglobulin preparations can be administered in one or more doses per day. Clinicians familiar with the diseases treated by IgG preparations can determine the appropriate dose for a patient according to criteria known in the art.

One commonly used IgG product, intravenous immunoglobulin or IVIG, is formulated for intravenous administration. Because the IgG preparation of this invention has achieved an exceptionally high immunoglobulin concentration (20% w/v or higher), which significantly reduces the volume for a therapeutically effective dose, the composition of the present invention are particularly advantageous for subcutaneous and/or intramuscular administration to a patient, even though intravenous administration remains an option for administration.

The term "effective amount" refers to an amount of an immunoglobulin, particularly IgG, preparation that results in an improvement or remediation of a medical condition being treated in the subject (e.g., primary immune deficiency, RRMS, Alzheimer's disease, Parkinson's disease, etc.). An effective amount to be administered to the subject can be determined by a physician with consideration of individual differences in age, weight, disease severity, route of administration (e.g., intravenous v. subcutaneous) and response to the therapy. In certain embodiments, an immunoglobulin preparation of this invention can be administered to a subject at about 5 mg/kilogram to about 2000 mg/kilogram each day. In additional embodiments, the immunoglobulin preparation can be administered in amounts of at least about 10 mg/kilogram, at last 15 mg/kilogram, at least 20 mg/kilogram, at least 25 mg/kilogram, at least 30 mg/kilogram, or at least 50 mg/kilogram. In additional embodiments, the immunoglobulin preparation can be administered to a subject at doses up to about 100 mg/kilogram, to about 150 mg/kilogram, to about 200 mg/kilogram, to about 250 mg/kilogram, to about 300 mg/kilogram, to about 400 mg/kilogram each day. In other embodiments, the doses of the immunoglobulin preparation can be greater or less. Further, the immunoglobulin preparations can be administered in one or more doses per day. Clinicians familiar with the diseases treated by IgG preparations can determine the appropriate dose for a patient according to criteria known in the art.

In certain embodiments, a concentrated IgG preparation can be administered to a subject at dose of about 5 mg/kilogram to about 2000 mg/kilogram per administration. In certain embodiments, the dose may be at least about 5 mg/kg, or at least about 10 mg/kg, or at least about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or at least about 2000 mg/kg.

In accordance with the present invention, the time needed to complete a course of the treatment can be determined by a physician and may range from as short as one day to more than a month. In certain embodiments, a course of treatment can be from 1 to 6 months.

The dosage and frequency of concentrated IgG treatment will depend upon, among other factors, the disease or condition being treated and the severity of the disease or condition in the patient. Generally, for primary immune dysfunction a dose of between about 100 mg/kg and about 400 mg/kg body weight will be administered about every 3 to 4 weeks. For neurological and autoimmune diseases, up to 2 g/kg body weight is implemented for three to six months over a five day course once a month. This is generally supplemented with maintenance therapy comprising the administration of between about 100 mg/kg and about 400 mg/kg body weight about once every 3 to 4 weeks. Generally, a patient will receive a dose or treatment about once every 14 to 35 days, or about every 21 to 28 days. The frequency of treatment will depend upon, among other factors. the disease or condition being treated and the severity of the disease or condition in the patient.

In a preferred embodiment, a method of treating an immunodeficiency, autoimmune disease, or acute infection in a human in need thereof is provided, the method comprising administering a pharmaceutical IgG composition of the present invention.

EXAMPLES

The following examples are provided by way of illustration only and not by way of limitation. Those of skill in the art will readily recognize a variety of non-critical parameters that could be changed or modified to yield essentially the same or similar results.

Example 1: Stability Study of Various IgG Concentrations and Formulations

1. Purpose

The purpose of this study is to compare the storage stability of the low pH (0.25M glycine pH 4.4-4.9 as measured in concentrated solution) at higher protein concentration with the neutral pH formulation (22.5 g/l glycine, 3 g/l NaCl pH 7) as currently used for intramuscularly and subcutaneously injectable immunoglobulins.

2. Experimental Design

All runs start with the concentration of the nanofiltrate to 5% protein. A ten times buffer exchange against 0.15M glycine (lowest glycine concentration investigated) is performed followed by the final concentration to a target value above 20% protein. While for the first set of experiments a 0.5 m$^2$ polyethersulfone Millipore membrane with molecular cut-off of 30K (regular screen) is used, the second set of experiments is done with a 0.5 m$^2$ polyethersulfone Millipore membrane with open screen, which is more suitable for solutions with higher viscosity and the post-wash fractions are concentrated by a second ultra-/diafiltration device with a lower membrane surface (0.1 m$^2$, open screen) in order to reduce yield losses.

The final containers are either formulated and stored at low pH or the low pH storage is done in bulk and afterwards they are formulated at neutral pH prior to storage.

TABLE 1

Overview of the ultra-/diafiltration steps (30K polyethersulfone membranes) and the final container pH

| | | | | |
|---|---|---|---|---|
| 0.5 m$^2$ ultrafiltration device | standard screen | standard screen | open screen | open screen |
| 0.1 m$^2$ ultrafiltration device | none | none | open screen | open screen |
| Final container pH | 4.7 | 7 | 4.7 | 7 |

3. Test Methods pH: pH was tested with Knick Portamess type 911 XPH equipped with a Mettler Toledo LoT405-DPA-SC-S8/120 electrode and a PT 1000 temperature probe.

Protein: Protein values were determined using Biuret.

Molecular size distribution was tested by using high performance size exclusion chromatography.

ACA titer was tested as described in the European Pharmacopoeia.

4. Acceptance Criteria

The following acceptance criteria are defined:

Molecular size distribution by HPLC:
  i. Monomers and Oligo-/Dimers: ≥90%
  ii. Aggregates: ≤10% (≤% for IV administration)
ACA titer:
  Less than 50% CH50 Units consumed/mg protein for IV administration.

5. Results and Discussion 5.1. Comparison of Aggregate and Fragment Content and ACA Titer in the Preparations Formulated at Low (pH 4.7 and at pH 7.0)

In the following Table 2, aggregate and fragment content as well as ACA titer after 3 months storage at 28 to 30° C. for the standard formulations (pH 4.7, 0.25M glycine; or pH 7.0, 22.5 g/L glycine, 3 g/L NaCl) at different protein concentrations are shown.

TABLE 2

Fragment, Aggregate and ACA values after 3 months storage at 28 to 30° C. at low pH and pH 7.0 at different protein concentrations

| | Fragments % | | Aggregates % | | ACA titer % | |
|---|---|---|---|---|---|---|
| Protein | pH 4.7 | pH 7.0 | pH 4.7 | pH 7.0 | pH 4.7 | pH 7.0 |
| 14% | 1.35 | 1.50 | 0.10 | 0.92 | 44.1 | 52.0 |
| 16% | 1.24 | 1.38 | 0.08 | 0.91 | 40.5 | 53.1 |
| 18% | 1.24 | 1.60 | 0.11 | 0.93 | 40.3 | 52.4 |
| 20% | 1.35 | 1.52 | 0.12 | 0.93 | 37.5 | 62.7 |

The data clearly show that the low pH formulation has lower aggregates and lower ACA-titer after 3 months storage at 28 to 30° C. All ACA titers of the pH 7 formulations are above the acceptance criterion defined for this test. In Table 2 the values after 3 months storage at 2 to 8° C. are given.

TABLE 3

Fragment, Aggregate and ACA values after 3 months storage at 2 to 8° C. at low pH and pH 7.0 at different protein concentrations

| | Fragments % | | Aggregates % | | ACA titer | |
|---|---|---|---|---|---|---|
| Protein | pH 4.7 | pH 7.0 | pH 4.7 | pH 7.0 | pH 4.7 | pH 7.0 |
| 14% | 0.36 | 1.80 | 0.16 | 1.09 | 38.3 | 46.5 |
| 16% | 0.30 | 0.51 | 0.11 | 1.01 | 37.4 | 44.7 |
| 18% | 0.33 | 1.10 | 0.17 | 0.86 | 35.8 | 39.8 |
| 20% | 0.33 | 1.98 | 0.20 | 1.06 | 36.1 | 46.0 |

The results at 2 to 8° C. confirm the trend seen at 28 to 30° C. The ACA titers are all below the limit defined as acceptance criteria although the pH 7.0 formulations seem to have higher values. The protein value does not influence the results of the parameters tested.

5.2 Influence of Different Concentration Procedures on Aggregate and Fragment Content as Well as ACA Titer in the Preparations IGSC60 (pH 4.7, A-Screen) and IGSC62 (pH 4.7, V-Screen, Post-Wash Concentration with Smaller UF-System)

In the following Table 4, aggregate and fragment content as well as ACA titer after 3 months storage at 28 to 30° C. for the low Ph formulations with different concentration procedures at different protein concentrations are shown.

TABLE 4

Fragment, Aggregate and ACA values after 3 months storage at 28 to 30° C. at low pH with different protein concentration methods

| | Fragments % | | Aggregates % | | ACA titer | |
|---|---|---|---|---|---|---|
| Protein | standard-screen | open-screen | standard-screen | open-screen | standard-screen | open-screen |
| 14% | 1.35 | 0.92 | 0.10 | 0.21 | 44.1 | 42.6 |
| 16% | 1.24 | 1.09 | 0.08 | 0.20 | 40.5 | 40.9 |
| 18% | 1.24 | 0.96 | 0.11 | 0.23 | 40.3 | 40.7 |
| 20% | 1.35 | 0.98 | 0.12 | 0.30 | 37.5 | 41.6 |

The data showed similar results after 3 months storage for both concentration modes. In Table 5 the corresponding values at 2 to 8° C. are shown

TABLE 5

Fragment, Aggregate and ACA values after 3 months storage at 2 to 8° C. at low Ph with different protein concentration methods

| | Fragments (%) | | Aggregates (%) | | ACA titer (%) | |
|---|---|---|---|---|---|---|
| Protein | standard-screen | open-screen | standard-screen | open-screen | standard-screen | open-screen |
| 14% | 0.36 | 0.27 | 0.16 | 0.17 | 38.3 | 39.6 |
| 16% | 0.30 | 0.22 | 0.11 | 0.14 | 37.4 | 38.3 |
| 18% | 0.33 | 0.23 | 0.17 | 0.18 | 35.8 | 39.6 |
| 20% | 0.33 | 0.22 | 0.20 | 0.20 | 36.1 | 39.9 |

The values obtained at 2 to 8° C. confirmed the results obtained at 28 to 30° C. The concentration method does not influence the stability of the product.

As the approach with two systems, one for the main concentration process and the other for the concentration of the post-wash, results in higher yield, this method was judged to be more appropriate for large scale manufacturing.

6. Conclusion

The following conclusions can be drawn from the results presented in this study:

The low pH formulation gives lower ACA values, lower aggregate and lower fragment contents after 3 months storage at 2 to 8° C. and 28 to 30° C.

After 3 months storage at 28 to 30° C. the ACA values of the neutral pH formulations are above the acceptance criteria.

The protein value does not influence the results of the parameters tested.

The concentration method does not influence the stability of the product.

Adequate post-wash can only be obtained with open-screen membranes

Based on these conclusions it was decided to produce the new IgG product for subcutaneous administration with the low pH formulation, the concentration method using a second smaller device for concentrating the post-wash, an ultra-/diafiltration device with open screen membranes and at a protein content of 20%±2%.

Example 2: Ultrafiltration and Formulation of SUB Q NG

1. Background

This information was gathered during production of scale-up and pre-clinical 20% lots. The process used for manufacturing of 20% lots until the nanofiltrate step was as described above. Ultra-/diafiltration was improved to concentrate the solution to 20% (limits: 18 to 22%). In order to reduce yield loss to a minimum, the post-wash of the ultrafiltration device used for diafiltration is concentrated by a second smaller device equipped with the same membranes and afterwards added to the bulk solution.

Surprisingly it could be shown that the virus inactivation during low pH storage is not influenced by the protein concentration of the solution. Similar virus reduction was achieved in 10% solution (GAMMAGARD® LIQUID) and in 20% solution. Therefore low pH storage as a virus reduction step was maintained for the 20% product.

2. Process Narrative

Ultrafiltration

The glycine concentration of the nanofiltrate is adjusted to a target of 0.25M. The solution is concentrated to a protein concentration of 6±2% w/v through ultrafiltration (UF). Typically, protein concentration is determined by measurement of $AU_{280-320}$. An extinction coefficient of 14.1 is used. The pH is adjusted to 5.2±0.2. The UF membrane used has a Nominal Molecular Weight Cut Off (NMWCO) of 50,000 daltons or less and is especially designed for high viscosity products (e.g., V screen from Millipore). For example, Millipore Pellicon Biomax with a NMWCO of 50K daltons or less. Membrane material is polyethersulphone.

The concentrate is diafiltered against a 0.25M glycine solution, pH 4.2±0.2. The minimum exchange volume is 10× of original concentrate volumes. Throughout the ultrafiltration/diafiltration operation, the solution is maintained at 4° C. to 20° C.

After diafiltration, the solution is concentrated to a protein concentration of minimum 22% w/v. The solution temperature is adjusted to 2° C. to 8° C. The protein concentration may be determined by UV reading through the use of an extinction coefficient value of 14.1

In order to recover the complete residual protein in the system, the post-wash of the first bigger ultrafiltration system is done with at least 2 times the dead volume in re-circulation mode to assure that all protein is washed out. Then the post-wash of the first ultrafiltration system is concentrated to a protein concentration of at least 22% w/v with a second ultra-/diafiltration system equipped with the same type of membrane which is dimensioned a tenth or less of the first one. The post-wash concentrate is added to the bulk solution. The second ultrafiltration system is then post-washed. This post-wash is used for adjustment of the protein concentration of the final bulk in step 14. The solution temperature is adjusted to 2° C. to 8° C.

Formulation

The protein concentration is further adjusted to 20.4±0.4% w/v with post-wash of the second smaller ultrafiltration system and/or with diafiltration buffer. The pH is adjusted to 4.4 to 4.9, if necessary.

Example 3: Manufacturing of 20% Lots

1. Introduction

This report describes the pre-clinical production and summarizes the results of Baxter's new investigational Immunoglobulin preparation "SUBQ NG, 20%," which is a 20% (w/v) liquid polyvalent human Immunoglobulin preparation for subcutaneous use.

The manufacturing was done as described in "Detailed Description of the Invention" with the concentration method as described above. Fractionation starts with the separation of cryo-precipitate. The cryo-poor plasma may then be used for isolation of various crude coagulation factors and inhibitors prior to subsequent cold alcohol fractionation. Seven pathways are chosen for batch adsorption of crude coagulation factors and inhibitors from the cryo-poor plasma prior to SUBQ NG, 20% purification and are referred to as pathways 1 to 7 in the following table.

TABLE 6

| Step | Gel | Heparin | Absorption Pathways | | | | | | |
|---|---|---|---|---|---|---|---|---|---|
| | | | 1 | 2 | 3 | 4 | 5 | 6 | 7 |
| Cryo-precipitation | — | — | X | X | X | X | X | X | X |
| FEIBA | 0.5 g DEAE-Sephadex/1 | — | | X | X | | | | |
| Factor IX | 0.5 g DEAE-Sephadex/1 | 2000 IU/ml | | | | X | X | X | X |
| Factor VII | 120 mg Al(OH)$_3$/1 | 750 IU/ml | | | | | | X | X |
| Antithrombin | 1 g DEAE-Sephadex/1 | 80000 IU/ml | | | X | | X | X | |

For pre-clinical SUBQ NG, 20% production Cohn starting materials derived from the pathways 1, 3 and 6 were chosen to cover a broad variety of different adsorption options. Various adsorption processes are described in Teschner et al., 2007, *Vox Sang.* 92:42-55; Polsler et al., 2008, *Vox Sang.* 94:184-192; U.S. Pat. Nos. 6,395,880 and 5,409,990; and *Prothrombin complex: Brummelhuis in Methods of Plasma Protein Fractionation* (J. M. Curling Editor, Academic Press, 1980).

The modified Cohn alcohol fractionation leads to a principal intermediate IgG fraction, referred to as Precipitate G, which is further processed to the final product using chromatographic purification. The downstream manufacturing comprises cation exchange (CM-Sepharose fast flow) and anion exchange chromatography (ANX-Sepharose fast flow) and includes three independent virus inactivation or removal steps, namely Solvent/detergent treatment (mixture of 1% Triton X-100, 0.3% Tri-N-butyl phosphate and 0.3% Polysorbate-80),
Nanofiltration (Asahi Planova 35 nm) and
Low pH storage for 3 weeks at elevated temperature.

In order to reach a higher protein concentration for subcutaneous application an open channel screen has to be used at the ultra-/diafiltration step. Preferably a second ultra-/diafiltration device is used for the concentration of the post-wash fraction in order to recover all protein from the first device.

SUBQ NG, 20% is a liquid formulation of Immunoglobulin G (IgG), of which at least 95% of the protein is gamma globulin. The product is isotonic and formulated at low pH. At a concentration of 10% protein during the final concentration step the pH is 4.4 to 4.9. The final pH of the 20% solution will be determined after the results of extended stability studies are available. The final solution contains 180 to 220 g protein and as the only excipient 0.1 to 0.3 moles of Glycine per liter solution. The liquid preparation is clear to slightly pale-yellow and substantially free of visible particles.

2. Data and Mass Balance of the Pre-Clinical Lots
  1. Pre-Clinical Lot: SC00107NG
    Adsorption Option 1: Option 6: F IX, F VII, AT-III
    Lot number of starting material: Precipitate G VNELG171 (US-source)
    Lot number of final container: SC00107NG
  2. Pre-Clinical Lot: SC00207NG
    Adsorption Option 3: FEIBA, AT-III
    Lot number of starting material: Precipitate G VNELG173 (US-source)
    Lot number of final container: SC00207NG 3. Pre-Clinical Lot: SC00307NG
Adsorption Option 1: no adsorption steps
Lot number of starting material: Precipitate G LB0790301 (US-source)
Lot number of final container: SC00307NG

TABLE 7

| Test/Method | Step Lot | Sterile Bulk | | |
|---|---|---|---|---|
| | | SC00107NG | SC00207NG | SC00307NG |
| Total/proteinUV | g/L Plasma | 3.4 | 3.7 | 3.7 |
| IgG/Nephelometric | g/L Plasma | 3.0 | 3.0 | 3.0 |
| IgA/ELISA | g/L Plasma | <0.001 | <0.001 | <0.001 |
| IgM/ELISA | g/L Plasma | <0.001 | <0.001 | <0.001 |
| MSD (HPLC) | % Aggregates | 0.1 | 0.1 | 0.1 |
| | % Oligo/Dimers | 4.6 | 4.5 | 3.2 |
| | % Monomers | 95.2 | 95.4 | 96.6 |
| | % Fragments | 0.1 | | 0.1 |

At the final bulk level the purity of the preparation is illustrated by the low levels of the main impurities, which are well below 0.1% of the total IgG. The molecular size distribution in the 20% product at this final stage of the process is similar to the one of a GAMMAGARD® LIQUID/KIOVIG final container. This indicates that the concentration to 20% protein has no negative impact on the integrity of the IgG molecule.

3. Additional Results from the Characterization of the Pre-Clinical Batches

The preliminary final container release criteria were defined on the basis of the requirements from the authorities for subcutaneous human immunoglobulins, the final container specifications of the current product for subcutaneous administration and the GAMMAGARD® LIQUID/KIOVIG specifications. Additional Quality Control tests were performed to evaluate the level of product and/or process related impurities.

Furthermore the characterization of the relevant Antibody Spectrum of the Final Containers was done and compared to the results from the pre-clinical IVIG, 10% TVR lots.

The results are given in the following table

TABLE 8

| | | | SUBQ NG 20% | | | IVIG, 10% TVR | | |
|---|---|---|---|---|---|---|---|---|
| | | | | | | P0010ING | P0020ING | P0030ING |
| | Test System | Unit | SC00107NG | SC00207NG | SC00307NG | 01C21AN11 | 0IC21AN21 | 01D05AN11 |
| Bacteria: | | | | | | | | |
| Cory nebacterium diphtheriae EUR | Guinea pigs | IU/ml | 6. | | | 5. | 5. | 5. |
| Viruses | | | | | | | | |
| HAV | ELISA | IU/ml | 14. | | | 14 | | 1 |
| HBV (antibody to hep B s Ag) | ELISA | IU/ml TP | 40. | | | 35.9 | 40.1 | 40. |
| Measles virus EUR Enrich. Factor | Hemagglut. | | 41. | | | n.a. | n.a. | n.a |
| Measles virus US | Hemagglut. | NIH 176 | 0.8 | | | 1.001 | 1.0 | 1.001 |
| Parvo 619 | ELISA | IU/ml | 718 | 78 | 71 | 567 | 442 | 36 |
| Poliomyelitis virus type I | | NIHU/ml | 1.4 | 1.711 | 1.5 | 1.01 | 1.11 | 1.21 |

The antibody titers and the enrichment factors are in the same order of magnitude for the three pre-clinical SUBQ NG 20% final containers and for the pre-clinical GAMMAGARD® LIQUID/KIOVIG lots.

TABLE 9

Quality Control Tests of SUBQ NG 20% Final Container

| | Test System | Unit | SC00107NG | SC00207NG | SC00307NG |
|---|---|---|---|---|---|
| Fc functional integrity | Bc-binding | % of BPR lot 3 | 15.8 | 138 | 164 |
| Anti-complementary activity | EP method | % | 41.1 | 41.5 | 41.2 |
| Anti-complementary activity | EP method | C'H50 U/mg | 41.4 | 41.8 | 41.6 |
| Prekallikrein activator activity, EUR | chromogenic | IU/ml | <0.6 | 1.004 | 1.237 |
| Anti-A hemagglutinins, pH. Eur. | hemagglut. | Dilution: 1: | 8 | 16 | 8 |
| Anti-B hemagglutinins, pH. Eur. | hemagglut. | Dilution: 1 | 4 | 4 | 2 |
| Anti-D | hemagglut. | | complies | complies | Complies |
| Exclusion of pyrogenicity, pH. Eur. and CFR | rabbit | ° C. rise | pyrogen free | pyrogen free | pyrogen free |
| Bacterial Endotoxins | Chromogenic | IU/ml | <1.2 | 1.8 | <1.2 |
| Purity by cellulose acetate electrophoresis | CAE | % | 99.6 | 99.8 | 99.5 |
| Molecular size distribution (Monomer + Dimers) | SE-HPLC | % | 99.2 | 99.3 | 99.2 |

TABLE 9-continued

Quality Control Tests of SUBQ NG 20% Final Container

| | Test System | Unit | SC00107NG | SC00207NG | SC00307NG |
|---|---|---|---|---|---|
| Molecular size distribution (Polymers) | SE-HPLC | % | 0.2 | 0.2 | 0.3 |
| Molecular size distribution (Fragments) | SE-HPLC | % | 0.6 | 0.5 | 0.5 |
| IgA - EUR | ELISA | µg/ml | 20 | 20 | 30 |
| IgM | ELISA | µg/ml | 1.1 | 1.0 | 1.2 |
| IgG | Nephelomnetry | mg/ml | 177 | 165 | 163 |
| Protein (Bulk) | UV | mg/ml | 201 | 203 | 202 |
| Protein | Autom. N2 | mg/ml | 202 | 208 | 203 |
| Glycine | HPLC | mg/ml | 14.7 | 14.5 | 14.7 |
| Polysorbate 80 | Spectrophot. | µg/ml | <250 | <250 | <250 |
| TNBP | Gas-chromat. | µg/ml | <0.3 | <0.3 | <0.3 |
| Octoxynol 9 | Ion-chromat. | µg/ml | <3 | <3 | <3 |
| Sterility | Membrane filtr. | NA | sterile | sterile | sterile |
| Osmolality | | mOsmol/Kg | 298 | 298 | 299 |
| pH, undiluted | Potentiometry | | 5.1 | 5.2 | 5.3 |
| Appearance | Visual Inspec. | | satisfied | satisfied | satisfied |
| Ethanol | Gas-chromat. | µg/ml | <20 | <20 | <20 |
| Isopropanol | Gas-chromat. | µg/ml | <20 | <20 | <20 |
| Aluminum AAS | Photometry | µg/L | <50 | <50 | <50 |
| Silicium ICP OES | Ion Electr. | µg/L | 3466 | 17270 | 21180 |
| Heparin | | IU/ml | <0.0075 | <0.0075 | <0.0075 |

The removal of product and process related impurities is satisfactory for all three lots.

4. Conclusions

Three final container lots of SUBQ NG 20% were successfully manufactured in the 200 liter scale. Three adsorption pathways were chosen to cover a broad variety of adsorption steps prior to alcohol fractionation, namely:

Option 1, US source plasma without adsorption steps
Option 3, US source plasma after FEIBA, AT-III adsorption
Option 6, US source plasma after F-IX, F-VII, AT-III adsorption In process parameters monitored during the pre-clinical production and the characterization of intermediates and the final product showed that there are no obvious differences detectable between the three lots.

All final containers meet the product related preliminary specifications regardless which kind of starting material was chosen.

Example 4: Storage Study of 20% Preparation

1. Introduction

SUBQ NG, 20% is a 20% (w/v) liquid polyvalent human Immunoglobulin preparation for subcutaneous use. The SUBQ NG, 20% was produced as described above.

This study summarizes the storage data of 3 preclinical lots and one feasibility lot at 2 to 8° C. and 28 to 30° C. (feasibility lot only) for up to 6 months.

2. Purpose

The purpose of this study is to evaluate the storage stability of Sub Q NG 20% final containers at 2 to 8° C. and 28 to 30° C.

3. Stability Indicating Parameters

The primary degradation modes are denaturation, aggregation and fragmentation, resulting in a change in the molecular size distribution of the sample. Therefore the molecular size distribution analysis by High Performance Size Exclusion Chromatography is the main stability indicating parameter.

4. Batches Examined and Primary Packaging

The stability data presented in this report are made with the pre-clinical lots SC00107NG, SC00207NG and SC00307NG as well as with the feasibility lot IgGSC 62/1.

5. Results

In the following Table 11 the results of the pre-clinical final containers after storage up to 12 months are shown.

TABLE 10

Stability of pre-clinical Sub Q 20% batches at 2 to 8° C.

| | | MSD (HP-SEC) (%) | | |
|---|---|---|---|---|
| Lot | Month | Aggregates (>450 KDa) | Olig/Dimers + Monomers | Fragments (<70 Kda) |
| SC00107NG | 0 | 0.3 | 99.5 | 0.2 |
| | 3 | 0.4 | 99.5 | 0.2 |
| | 4 | 0.5 | 99.4 | 0.2 |
| | 6 | 0.5 | 99.3 | 0.2 |
| | 12 | 0.7 | 99.1 | 0.3 |
| SC00207NG | 0 | 0.3 | 99.5 | 0.2 |
| | 3 | 0.4 | 99.5 | 0.1 |
| | 4 | 0.5 | 99.3 | 0.2 |
| | 6 | 0.6 | 99.2 | 0.2 |
| | 12 | 0.8 | 99.0 | 0.2 |
| SC00307NG | 0 | 0.3 | 99.6 | 0.1 |
| | 3 | 0.5 | 99.3 | 0.2 |
| | 4 | 0.6 | 99.2 | 0.1 |
| | 6 | 0.7 | 99.1 | 0.2 |
| | 12 | 0.9 | 98.8 | 0.2 |
| Release criteria | | <5 | >90 | <5 |

TABLE 11

Stability of the feasibility lot IgGSC 62/1 at 2 to 8° C. and 28 to 30° C.

| | | | MSD (HP-SEC) (%) | | |
|---|---|---|---|---|---|
| Lot | ° C. | Month | Aggregates (>450 KDa) | Olig/Dimers + Monomers | Fragments (<70 Kda) |
| IgGSC 62/1 | 2 to 8 | 0 | 0.2 | 99.5 | 0.3 |
| | | 1 | 0.1 | 99.7 | 0.2 |
| | | 3 | 0.2 | 99.6 | 0.2 |

TABLE 11-continued

Stability of the feasibility lot IgGSC 62/1 at
2 to 8° C. and 28 to 30° C.

| Lot | ° C. | Month | MSD (HP-SEC) (%) | | |
|---|---|---|---|---|---|
| | | | Aggre-gates (>450 KDa) | Olig/Dimers + Monomers | Frag-ments (<70 Kda) |
| | | 6 | 0.3 | 99.4 | 0.3 |
| | | 12 | 0.4 | 99.3 | 0.3 |
| | | 18 | 0.4 | 99.2 | 0.4 |
| | 28 to 30 | 0 | 0.2 | 99.5 | 0.3 |
| | | 1 | 0.2 | 99.2 | 0.6 |
| | | 3 | 0.3 | 98.7 | 1.0 |
| | | 6 | 0.6 | 98.0 | 1.4 |
| | | 12 | 1.2 | 95.6 | 3.2 |
| | | 18 | 1.9 | 93.5 | 3.8 |
| Release criteria | | | <5 | >90 | <5 |

6. Conclusion

The data confirmed that the product complies to the pre-defined specifications for the parameters investigated for up to 18 months storage at 2 to 8° C. and 28 to 30° C.

Example 5: Low pH Treatment for Viral Inactivation

Purpose and Rationale
Introduction

Immune Globulin Subcutaneous (Human), 14%-20%, Triple Virally Reduced (TVR) Solution, in the following called Subcuvia NG Solution, is manufactured from pooled human plasma. After mass capture steps to remove coagulation factors/inhibitors, purification of Subcuvia NG starts with a modified Cohn alcohol fractionation, leading to a principal intermediate precipitate G, followed by a downstream process which contains chromatographic purification as well as three distinct virus inactivation/removal steps. In the current study, the virus reduction capacity of the low pH storage of the final container was investigated in detail.

Figure 2:
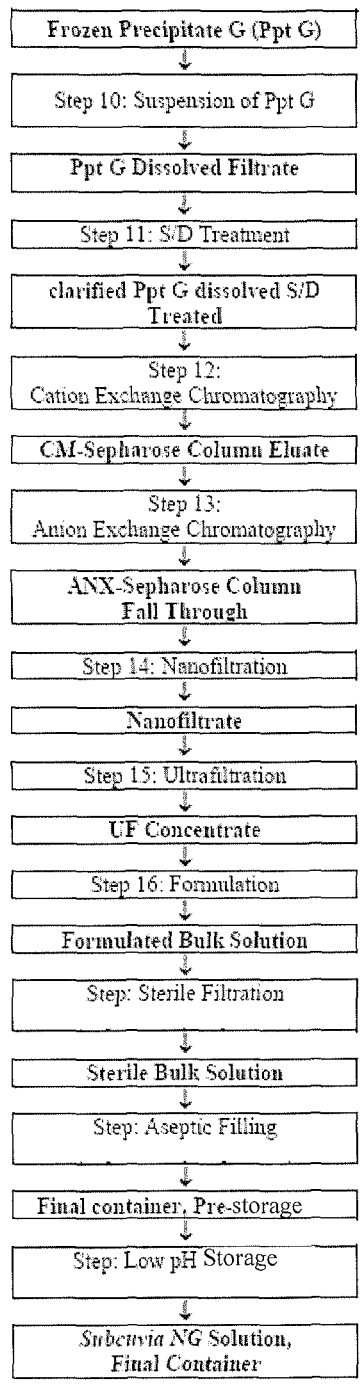
FIG. 2 provides an overview of the downstream part of the manufacturing scheme for Subcuvia NG Solution starting with Step 10. As described further in Example 5, viral inactivation by low pH treatment was assayed according to the sampling plan shown under process scheme B. Briefly, a sample was drawn for BVDV and MMV testing after the virus spike, "SSM." A second sample was drawn for BVDV and MMV testing after the virus spike and then filtered using a 0.45 µm PVDF membrane, "SSM filt." After pH adjustment and filtration in scheme B, a first sample was drawn for BVDV and MMV testing as soon as the temperature reached 29° C., "0 d." Subsequent samples were drawn after storage for 7, 14, 20, and 27 days at 30° C.±1° C., "7 d," "14 d," "20 d," and "27 d," respectively. Additional samples for bulk titration of BVDV were drawn after storage for 20 and 27 days "20 d Bulk 0," "20 d Bulk −0.5," "20 d Bulk −1," "27 d Bulk 0," "27 d Bulk −0.5," and "27 d Bulk −1."
Figure 2:
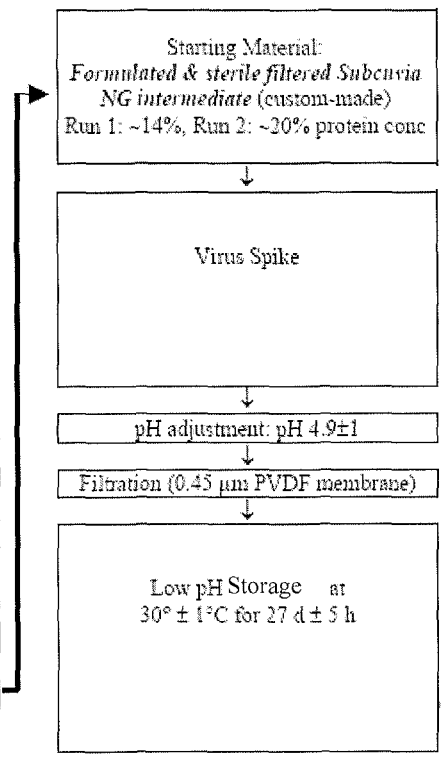

The downstream purification process comprises the following steps: resuspended Precipitate G is subjected to Solvent/Detergent (S/D) treatment, cation exchange chromatography using Carboxymethyl(CM)-Sepharose fast flow and anion exchange chromatography using ANX-Sepharose® fast flow, nanofiltration, ultra-diafiltration, pH adjustment, and sterile filtration and filling. After aseptic filling the Subcuvia NG Solution is subjected to low pH storage in the final container (for schematic illustration of the manufacturing process, see process scheme below).
Process Scheme Process scheme A, shown in FIG. 2, provides an overview of the downstream part of the manufacturing scheme for Subcuvia NG Solution starting with Step 10. The custom-made intermediate used in the current study is equal to the process step "Final container, Pre-storage."

Process scheme B, shown in FIG. 2, provides an overview of the downscaled process used in the present study including sample drawing for virus titration.
Purpose To provide a high safety margin with respect to a potential virus transmission, three dedicated virus inactivation/removal steps, which complement each other in their mode of action, are integrated into the manufacturing process of Subcuvia NG Solution:
  Solvent/Detergent treatment (step 11)
  Nanofiltration (step 14)
  Low pH Storage at elevated temperature in the final container (post-aseptic filling)

The capacity and robustness of the storage at low pH and elevated temperature with respect to inactivation of viruses was already investigated in the course of a previous study, in which IGIV 10% TVR, a product equivalent to Subcuvia NG but adjusted to 10% protein for i.v. application, was used. The results obtained from this study demonstrated that all lipid-enveloped viruses investigated were effectively and robustly inactivated, with Bovine viral diarrhea virus (BVDV) showing the slowest inactivation kinetics. Moreover, it could be demonstrated that this process step further contributes to the viral safety of the manufacturing process with regard to small non lipid-enveloped DNA viruses. Subcuvia NG and IGIV 10% TVR are immunoglobulin products, where Subcuvia NG is the variation for subcutaneous administration, and IGIV 10% TVR is the product variation for i.v. application. Both share the same manufacturing process up to the ultrafiltration/diafiltration and formulation steps, where the only difference is that the protein concentration of Subcuvia NG is adjusted to a range of 14% to 20% instead of 10%.

Therefore the capacity and robustness of the storage step at low pH and elevated temperature in the manufacture of Subcuvia NG (see, The European Agency for the Evaluation of Medicinal Products Evaluation of Medicines for Human Use (2001): CPMP Biotechnology Working Party—Note for Guidance on Plasma-Derived Medicinal Products, CPMP/BWP/269/95 (rev. 3)) with respect to inactivation of BVDV and MMV was evaluated by setting selected critical process parameters to the upper and lower limits specified for the manufacturing process (i.e., time, temperature: lower limit; pH: upper limit). In addition, to further investigate the robustness of this virus inactivation step, the temperature was reduced for a given time period during the downscaled runs.

As discussed above, the following enveloped and non-enveloped viruses were used.
  Bovine viral diarrhea virus (BVDV) as a model for hepatitis C virus (HCV) and for other small lipid-enveloped RNA viruses.
  Mice Minute Virus (MMV) as a model for Human Parvovirus B19 (B19V) and for other small non-enveloped DNA viruses.

In accordance with the CPMP guideline 268/95 (The European Agency for the Evaluation of Medicinal Products Human Medicines Evaluation Unit (1996): CPMP Biotechnology Working Party—Note for Guidance on Virus Validation Studies: The Design, Contribution and Interpretation of Studies Validating the Inactivation and Removal of Viruses, CPMP/BWP/268/95 (revised)) the study was conducted with a downscaled model of the respective manufacturing step. The validity of the results obtained with the scaled-down manufacturing step "Storage at low pH and elevated temperature" with regard to virus inactivation in the manufacture of Subcuvia NG Solution, was demonstrated by comparison of parameters specified for this manufacturing step in the large-scale production process and process parameters of the downscaled model. Additionally, selected biochemical parameters were monitored and compared to the respective parameters of the large-scale process.
Materials, Methods and Equipment
Viruses and Cells BVDV, strain NADL (biologically cloned, ATCC VR-1422), obtained from the American Type Culture Collection (ATCC; Rockville, Md.) is used. The virus is propagated on MDBK cells (ATCC CCL-22), according to standard operating procedures, and titrated on BT cells (ATCC CRL-1390).

MMV, prototype strain (ATCC VR-1346), was obtained from the American Type Culture Collection, Rockville, Md. The virus was propagated according to standard operating procedures and titrated on A9 cells (ATCC CCL-1.4).

Test Item

The following lots of custom-made Subcuvia NG intermediate, before "Storage at low pH and elevated temperature", i.e., after manufacturing step aseptic filling, were obtained from Baxter's PPD Product Support department, Industriestrasse 131, Vienna, Austria:
Lot number IGSC64, with a protein concentration of 13.5%
Lot number IGSC64, with a protein concentration of 20.90/%

The material was shipped in the final container at +2° C. to +8° C. and was used within 6 months.

Buffers/Solutions
Solutions for pH Adjustment

The pH was adjusted using 0.5 M NaOH or 0.5 M HCl. (Both solutions were stored at room temperature and used within 12 months).

Preparation of 0.5 M Hydrochloric Acid (HCl)

| Component | Component per liter solution | Shelf life | Storage |
|---|---|---|---|
| HCl 37% | 41.4 ± 0.4 ml | 12 months | 23 ± 5° C. |

Reagents, i.e. aqua dest. and HCl were combined at ambient temperature.

Preparation of 0.5 M Sodium Hydroxide (NaOH)

| Component | Component per kg of aqua dest. | Shelf life | Storage |
|---|---|---|---|
| NaOH | 20.0 ± 0.2 g | 12 months | ±5° C. |

The respective amount of NaOH was dissolved in aqua dest. at ambient temperature.

Solutions for pH Measurement pH was measured both directly and in a diluted solution according to the European Pharmacopoeia (EP). For measuring pH according to the EP method, the protein concentration was diluted to 1% using a 0.9% NaCl solution.

The 0.9% NaCl solution was prepared as follows: 9.0±0.9 g NaCl were dissolved in 1000 ml aqua dest. The solution was 0.2 μm filtered, stored at room temperature and used within 12 months.

Cell Culture Media

Media used for cell culture or virus titration were prepared according to standard operating procedures for BVDV and MMV viral titration.

Virus Titration Assays $TCID_{50}$ Assay

Samples containing viruses were titrated by $TCID_{50}$ assays according to standard operating procedures. Briefly, serial ½ log dilutions of the samples were prepared in the respective tissue culture medium, and 100 μl of each dilution were added to each of 8 wells of a microtiter plate seeded with the respective indicator cell line. The microtiter plates are stored in humidified and $CO_2$-regulated storage units at a temperature of 36° C.±2° C. Evaluation of cytopathic effects is accomplished by visual inspection of the cells under a microscope after 7 days of storage.

Median tissue culture infectious doses ($TCID_{50}$) were calculated according to the Poisson distribution and expressed as $\log_{10}$ [$TCID_{50}$/ml].

BVDV Bulk Titration

Studies were performed on MMV-spiked samples. In order to lower the limit of detection for the BVDV spiked samples taken from the Subcuvia NG intermediate after 20 and 27 days of low pH storage, these samples were titrated as follows: in addition to the standard $TCID_{50}$ assay, samples of the 1:3.16 dilution (0.5 logs) and following two ½ log dilutions (the respective cell culture medium is used for dilution) are added to all wells (100 μl per well) of 96-well microtiter plates seeded with the respective indicator cell line. Storage of cells and evaluation of the cytopathic effect of the respective virus are done as described above ($TCID_{50}$ Assay). The results were calculated as follows: The ratio $R_{Vol}$ of the volume titrated in the bulk titration and the volume titrated in the regular $TCID_{50}$ assay was calculated. The $\log_{10}$ of RVol is subtracted from the virus titer determined in the $TCID_{50}$ assay, and the result is given as the virus titer determined by bulk titration.

Example

A sample is assayed ($TCID_{50}$ assay) on a microtiter plate in serial 0.5 log dilutions (all 12 columns) and the wells are found negative from the dilution 0 (i.e. undiluted) onwards. Calculation according to the Poisson distribution gives a virus titer of <0.11 $\log_{10}$ [$TCID_{50}$/ml]. The corresponding total volume of the sample assayed is 1.17 ml.

The same sample (dilution 0) is applied onto all wells of a microtiter plate (bulk titration). Therefore, the total sample volume applied is 9.6 ml The ratio of volumes is: $R_{Vol}$=9.6:1.17=8.21; $\log_{10}$ ($R_{Vol}$)=0.91.

The calculated virus titer is then <0.11-0.91; i.e. <−0.80. The upper limit of the virus titer's confidence interval is calculated identically.

Calculation of Virus Titer when No Infectivity is Scored in Successive Kinetic Samples Where no viral infectivity was detected in successive kinetic samples up until the final sample after completion of low pH storage, the volume of all successive negative samples used for wells in the $TCID_{50}$ assay with a clear negative result ass taken into account for calculation of the assay detection limit. For this the following formula was used (see also Appendix 1):

$$\text{Virus titer based on } n \text{ negative successive kinetic samples, } [\log_{10}(TGCID_{50}/\text{ml})] = < -\log_{10}\left(\sum_{i=1}^{n} 1/10^{X_i}\right)$$

with
$X_i$ (i=1, 2, 3, ... n) individual virus titers [$\log_{10}(TCID_{50}$/ml)] of n successive negative samples If all negative samples have the same titer, i.e. x, the formula simplifies to:
Virus titer based on n negative successive kinetic samples, [$\log_{10}(TGCID_{50}$/ml)]=<x−$\log_{10}$(n)

Cytotoxicity

The cytotoxicity of process intermediates for the virus indicator cell lines used was determined from mock-spiked Subcuvia NG intermediate, i.e. spiked with BT-medium for infected cells (5% Horse serum)* instead of virus stock as well as from mock-spiked, pH adjusted (pH 4.9±0.1) and 0.45 µm filtrated starting material on each cell line for determination of cytotoxicity. Samples were assayed like virus-containing samples, i.e. they were serially diluted and Stored with the indicator cell line. After storage, the highest non-cytotoxic concentration was determined. With regard to variations in these biological systems, deviations of ±0.5 log steps were considered non-significant when comparing cytotoxicity in virus spiked and mock-spiked samples.

* The composition of the BT-medium for infected cells is as follows: DMEM (containing 4.5 g/l D-Glucose)+1% (v/v) L-Glutamine (200 mM)+1% (v/v) Gentamicin Sulphate (10 mg/ml)+1% (v/v) Sodium Pyruvate+2% (v/v) Sodium Bicarbonate (7.5%)+1% (v/v) non-essential amino acids+5% (v/v) Horse serum.

Interference

For samples with low virus titers, the influence of the sample matrix on the performance of the infectivity assay needs to be assessed. For samples containing high virus titers, the relevant part of the dilution series, i.e. the part where virus-positive and virus-negative wells can be scored, occurs at high sample dilutions. Consequently, the influence of the sample matrix, which is also diluted several $\log_{10}$ steps, on the detection of virus infectivity can be neglected. The interference with determinations of low viral titers for samples containing Subcuvia NG intermediate was measured as follows: Samples were drawn from the mock-spiked, pH adjusted (pH 4.9±0.1) and 0.45 µm filtrated starting material (Subcuvia NG intermediate), diluted 1:3.16 with the appropriate tissue culture medium and spiked 1:100 with pre-diluted (in appropriate tissue culture medium, i.e. BT medium for BT cells/BVDV and A9 medium for A9 cells/MMV) virus stock suspension to a nominal titer of 2 or 3 $\log_{10}$ [$TCID_{50}$/ml] and titrated as described above. The titers obtained for spiked process intermediates were compared to those of spiked cell culture medium controls.

Calculation of Virus Reduction Factors

The analysis of the virus inactivation capacity of the process was carried out according to CPMP guideline 268/95 [3], using the following formula:

$$R = \log\left(\frac{V_1 x T_1}{V_2 x T_2}\right)$$

where,
R=virus reduction factor
V1=volume of starting material
T1=concentration of virus in starting material [$TCID_{50}$/ml]
V2=volume of material after the step
T2=concentration of virus after the step [$TCID_{50}$/ml]

The volumes and the titers of each spiked sample before and after treatment were used to calculate R. Whenever virus was undetectable, the detection limit was taken as the virus titer for calculation. According to standard operating procedures, calculations were carried out with virus titers ($\log_{10}$ [$TCID_{50}$/ml]) given to two decimal places; reduction factors were rounded to the first decimal place.

Determination of Validation Parameters

Time, Temperature [° C.]

Storage time was measured with timers; the temperature was measured with Pt-100 sensors and recorded continuously.

pH-Value

The pH value was determined according to standard operating procedures with a standard laboratory pH meter by direct measurement as well as implementing the method specified by the European Pharmacopoeia (EP), i.e. after dilution to 1% protein with 0.9% NaCl solution. In the following, pH with suffix (EP) means pH measurement according to EP method, whereas "pH" without suffix means direct measurement.

Determination of Other Parameters

Molecular Size Distribution (MSD)

HPLC-SEC (High-Performance Liquid Chromatography-Size Exclusion Chromatography) analysis of molecular size distribution was done by the department Analytical Biochemistry, Baxter, Vienna, Austria, according to standard operating procedures. The HPLC-SEC analysis of all samples of the "scale-up" lots (produced in the department PPD Product Support, Baxter, Vienna, Austria) were performed according to this test. Thus, to assure comparability between the test results of the samples of the mock-spiked runs (accumulated in the downscaled process in the course of this study) and the test results of the "scale-up" lots, the analysis of MSD of the samples of the mock-spiked runs were done according to the same test in the same department.

Cellulose Acetate Electrophoresis

Cellulose Acetate Electrophoresis (CAE) was performed according to standard operating procedures by the department ACV Chemistry, Baxter, Vienna, Austria.

Rounding

Rounding was performed according to standard practices:
Assay results were rounded to the same number of decimal places as specified for the respective parameter in the manufacturing process, or as determined by the accuracy of the assay.
Calculations were done without rounding of assay results, and only the final result was rounded.

Equipment

A standard laboratory pH-meter was used.
A Mettler AT-100 analytical and a Sartorius BP3100P laboratory balance were used.
0.45 µm filtration was performed with PVDF membrane filters (Millex-HV, or equivalent).
The process time was measured with laboratory timers.
Biosafety class II cabinets were used.
Cells were stored in humidity-controlled Heraeus $CO_2$-incubators.
Magnetic stirrers/stirring bars were used for mixing.
Temperature was controlled by Haake or Julabo cryostats and/or a stirring heating block.
Temperature was measured using Pt-100 sensors connected to a µR 1000 YOKOGAWA recorders.

Study Design

In order to investigate the robustness of manufacturing step "Storage at low pH and elevated temperature" of Subcuvia NG with respect to virus inactivation, key parameters for the efficacy of virus inactivation were defined as discussed below. Runs were performed under conditions suitable to investigate the robustness of virus inactivation by low pH storage. A comparison of the conditions for the large-scale process and the downscaled runs is given in Table A.

Protein concentration: As Subcuvia NG is a developmental product, the protein concentration range for the formulated bulk is currently rather broadly defined, i.e. approximately 14% to 20%, and might be narrowed down later on. Thus, to investigate the robustness of the low pH treatment, two runs (run designs) were performed at the two extremes of possible protein concentrations. Run design 1 was performed at 13.5% protein concentration; Run design 2 was performed at 20.9% protein concentration.

The protein concentration of the custom-made material was provided by the department PPD Product Support. The protein concentration of the custom-made material was not determined again, as data were already available from analyses, performed after production of the custom-made Subcuvia NG intermediate. Since the material, which was used for the down-scaled process, was sterile filtered and stored at 2° C. to 8° C. until the start of the down-scaled process (i.e., not subjected to any freeze/thaw procedure), no change in the protein concentration is anticipated for the finally formulated and sterile filtered intermediate.

pH-Value: In production, a pH range of 4.4-4.9 (direct measurement) is specified for the Subcuvia NG final container throughout the low pH storage. To investigate the efficacy and robustness of the low pH treatment under conditions less favorable for virus inactivation both runs were performed at the higher limit specified, i.e., a pH of 4.9±0.1. The pH was measured after spiking and adjusted to the higher limit, if necessary. After the low pH storage for 27 days±5 hours, the pH was measured again by direct pH-measurement and by the method recommended by the European Pharmacopoeia, i.e., dilution to 1% protein with 0.9% NaCl solution.

Temperature: In the production process the temperature during low pH storage is set to 30-32° C. To investigate the robustness of the low pH storage under conditions less favorable for virus inactivation, all downscaled runs were performed at the lower limit of the temperature range, i.e., at 30±1° C. To examine the potential impact of temperature fluctuations, the temperature was reduced to 25±1° C. for ≥6 hours once every week (i.e., decrease in temperature was started during day 0, 7, 14, 20 and day 27 of storage; numbering of days refers to calendar days, i.e. day 0 is the day on which the storage is started). Erroneously, the decrease in temperature to 25±1° C. for 6 hours was performed twice per week in the first and in the second week of storage, i.e., during day 0 and 4 of storage in the first week and during day 7 and 10 of storage in the second week of the low pH treatment.

Time: The storage time is typically in the range of 21 days (required for effective inactivation of BVDV) to 28 days (upper limit for technical/logistical reasons). To investigate the efficacy and robustness of the low pH treatment under conditions less favorable for virus inactivation all downscaled runs were performed below the limits of the above listed storage time range; i.e. for 20 days±4 hours for the short option and storage for 27 days±5 hours for the longer option. The spiked intermediate was stored at low pH and elevated temperature for 27 days±5 hours, but samples for virus titration were drawn after 20 days±4 hours of storage, in order to investigate virus clearance after 3 weeks of storage (see also Table A).

Overall, a total of 4 virus-spiked runs (2 with BVDV, and 2 with MMV) were performed to investigate the robustness of the virus inactivation capacity of manufacturing step "Storage at low pH and elevated temperature." Furthermore, two unspiked control runs were performed to generate samples for determination of biochemical parameters. In addition, two mock-spiked control runs were performed and samples taken from these runs were used to investigate potential effects (i.e., cytotoxicity and interference) of process intermediates on the virus titration assay.

To further demonstrate the equivalence of the downscale and the large scale processes, the following biochemical analyses were performed on the final product before and after low pH storage: molecular size distribution and cellulose acetate electrophoresis.

TABLE A

Process and biochemical parameters of the down scale runs, compared to the large-scale manufacturing process. Parameters, where ranges different from the large-scale process apply for the downscaled process, are in bold print.

| | | down-scaled process | |
|---|---|---|---|
| Parameter | large-scale process | Run design 1 | Run design 2 |
| Before spiking and pH adjustment | | | |
| Protein concentration [g/100 ml] | 14 to 20[1] | 14 ± 1[1] | 20 ± 1[1] |
| After spiking and pH adjustment | | | |
| pH (direct measurement) | 4.4-4.9 | 4.9 ± 0.1 | 4.9 ± 0.1 |
| Low pH storage | | | |
| Storage period [d] | 21-28[2] | 20 d ± 4 h[3] | 20 d ± 4 h[3] |
| | | 27 d ± 5 h[3] | 27 d ± 5 h[3] |
| Temperature during storage [° C.] | 30-32 | 30 ± 1[4] | 30 ± 1[4] |
| After low pH storage | | | |
| pH (direct measurement) | 4.4-4.9 | as measured (not specified) | |
| pH (diluted to 1% protein with 0.9% NaCl) EP[5] | 4.6-5.1 | as measured (not specified) | |

[1]As Subcuvia NG is a developmental product, the protein concentration is not narrower defined yet. Thus, the two down-scaled runs were performed at the two extremes of possible protein concentration.
[2]The storage period is not narrower defined yet, as dependent on the outcome of the virus clearance studies.
[3]Both runs were performed for 27 d ± 5 h and samples for virus titration were taken on day 20 of storage so that virus inactivation data were also available for the large scale process option of 21 to 22 days of storage.
[4]The temperature was reduced to 25 ± 1° C. for • 6 hours once every week (i.e. decrease in temperature was started during day 0, 7, 14, 20 and day 27; numbering of days refers to calendar days, i.e. day 0 is the day on which the storage is started) of storage. As discussed in Section 4.1.1 ("Temperature profile"), the decrease in temperature to 25 ± 1° C. for 6 hours was erroneously performed twice per week in the first and in the second week of storage (see also DR1_0407).
[5]Method according to the European Pharmacopoeia.

Experimental Procedure

Figure 3:
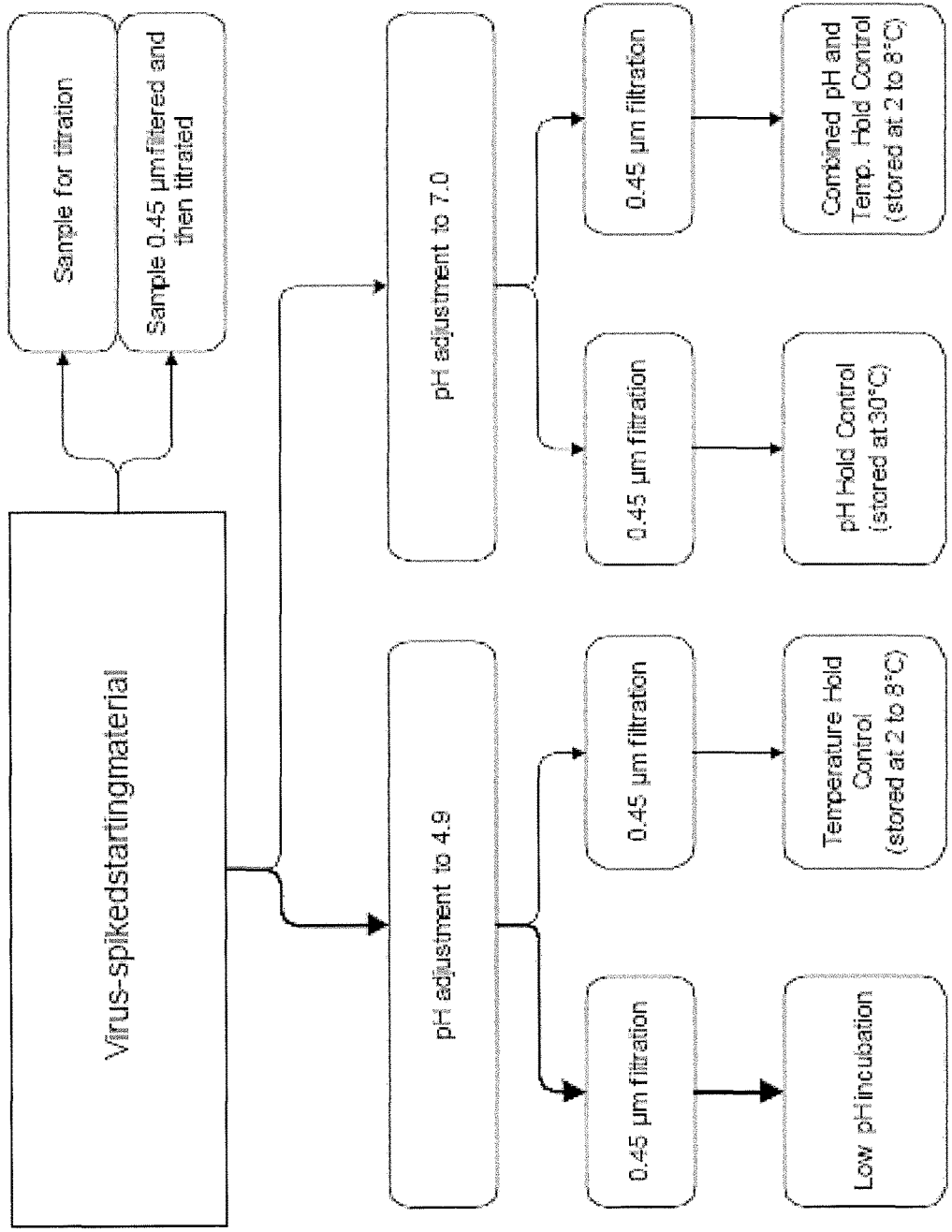
FIG. 3 illustrates the sequence of virus spike, pH adjustments and 0.45 mm filtration steps.

Due to its complexity, the sequence of virus spike, pH adjustments and 0.45 mm filtration steps is illustrated in the flow chart found in FIG. 3 (thickness of arrows indicates relative volumes).

Starting Material

For Run 1 custom-made material (Lot number IGSC64) with a protein concentration of 13.5% was taken. This material was used to perform runs at the lower limit of the possible protein concentration, at the upper limit of the pH range (i.e., BVDV: 4.97 and MMV: 4.93) and at the lower limit of the temperature range (i.e., at 29.4° C.).

For Run 2 custom-made material (Lot number IGSC64) with a protein concentration of 20.9% was taken. This material was used to perform runs at the upper limit of the possible protein concentration, at the upper limit of the pH range (i.e., BVDV: 4.92 and MMV 4.86) and at the lower limit of the temperature range (i.e., 29.4° C.).

Virus Spike: BVDV, MMV
  Storage
  45.5 ml of each starting material was spiked with 4.5 ml of virus stock suspension, and a 1 ml-sample was drawn after 1 to 2 minutes of stirring. The sample was diluted immediately 1:3.16 (i.e., 1 volume of sample plus 2.16 volumes of cell culture medium) with the respective cell culture medium and titrated. Subsequently, another 3 ml sample was drawn and filtered through a 0.45 μm PVDF membrane. One ml of the filtered material was diluted immediately 1:3.16 with the respective cell culture medium and titrated.

Adjustment of pH

An aliquot of 35 ml of the virus spiked starting material was adjusted to a pH of 4.9±0.1 (both runs) using a 0.5 M HCl solution under stirring. The material was then divided into two aliquots. One aliquot of 30 ml was used for the "Low pH Storage" and a 5 ml aliquot was used for the "temperature hold control" (see section "Hold Controls").

Another aliquot of 10 ml of the virus-spiked starting material was adjusted to a pH of 7.0±0.1 using a 0.5 M NaOH solution, where 5 ml of the pH-adjusted material were used for the "pH Hold Control".

The remaining 5 ml of the pH adjusted material were used for the "Combined pH and Temperature Hold Control" (see section "Hold Controls").

Hold Controls

To investigate the mechanism of virus inactivation, i.e. by pH or by temperature, three hold controls were stored under different conditions:

Each of the 5 ml-aliquots of the virus-spiked and pH adjusted (pH 7.0±0.1) starting material were filtered through a 0.45 μm PVDF membrane filter into a cryovial. One aliquot was stored at 30±1° C., together with the spiked process material and then kept at this temperature until the end of the process (pH Hold Control, "pH HC"). The other aliquot was immediately stored at +2° C. to +8° C. for 27 days±5 hours (Combined pH and Temperature Hold Control, "c HC").

The 5 ml-aliquot of the virus-spiked, pH-adjusted (pH 4.9±0.1) and 0.45 μm filtered starting material (see above "Adjustment of pH") was immediately stored at +2° C. to +8° C. until the end of the process (Temperature Hold Control. "t HC").

The minimum volume of all Hold Controls after filtration was always more than 3 ml, thus, a proper volume for virus titration after the storage period was available.

Low pH Storage

The 30 ml-aliquot of the virus spiked and pH adjusted (pH 4.9±0.1) Subcuvia NG intermediate was filtered through a 0.45 μm PVDF membrane filter into a 50 ml sterile glass bottle. The minimum volume of the Subcuvia NG intermediate after filtration was always more than 24 ml. Thus, enough volume for virus titration after the storage period was available. Subsequently, the temperature was equilibrated to 30±1° C. under agitating back and forth in slow motion using a water bath, with the water bath regulated by a temperature controlled cryostat via an external temperature sensor. The external temperature sensor and an additional Pt 100 electrode were placed into one 50 ml glass bottle equivalent to those used for the low pH storage, each of them filled with 30 ml water, which was the maximal possible amount of spiked process material after filtration. The temperature was recorded continuously. As soon as the material reached a temperature of 29° C., sample taking was initiated. Each sample was immediately diluted 1:3.16 (i.e. 1 volume of sample plus 2.16 volumes of cell culture medium) with the respective cold cell culture medium (stored at +2° C. to +8° C.) to prevent further inactivation of virus by low pH, and titrated. In all runs the Subcuvia NG intermediate was stored under agitation (back and forth in slow motion) at 30±1° C. throughout the whole process for 27 days±5 hours, with a reduction of the temperature to 25±1° C. for at least six hours (≥6 h) once every week of storage. Erroneously, the decrease in temperature to 25±1° C. for 6 hours was performed twice per week in the first and in the second week of storage, i.e. during day 0 and 4 of storage in the first week and during day 7 and 10 of storage in the second week of the low pH treatment. For discussion, please refer to Section 4.1.1 ("Temperature profile"). Further samples were drawn according to the sampling plan (see Section 3.2), immediately diluted as described above and titrated. After completion of the low pH storage at 30° C.±1° C., the pH was determined by direct measurement and by the method recommended by the European Pharmacopoeia (i.e., dilution to 1% protein with 0.9% NaCl solution).

Control Run without Virus

Two control runs were performed as described for the virus-spiked runs, where unspiked and 0.45 μm filtrated Subcuvia NG intermediate is processed. The same process parameters apply as specified for the virus-spiked Runs 1 and 2, respectively, except that the material was not pH adjusted. Samples for determination of biochemical parameters were taken according to the sampling plan (see Section 3.2).

The cytotoxicity of the mock-spiked starting material (spiked 0.9:10 with BT-medium for infected cells*; sample is filtered as described above before titration) and the mock-spiked and pH adjusted Subcuvia NG intermediate after 0.45 μm filtration was determined. Samples for determination of cytotoxicity were taken according to the sampling plan (see Section 3.2).

* The composition of the BT-medium for infected cells is as follows: DMEM (containing 4.5 g/l D-Glucose)+1% (v/v) L-Glutamine (200 mM)+1% (v/v) Gentamicin Sulphate (10 mg/ml)+1% (v/v) Sodium Pyruvate+2% (v/v) Sodium Bicarbonate (7.5%)+1% (v/v) non-essential amino acids+5% (v/v) Horse serum.

Potential Interference

The interference of the sample matrix for samples containing Subcuvia NG intermediate after pH adjustment (pH 4.9±0.1) with the detection of viruses was investigated in duplicate for each indicator cell line as follows: a sample of 1 ml, drawn from the mock-spiked pH adjusted and 0.45 μm filtered Subcuvia NG intermediate, was diluted 1:3.16 (v/v) with the respective cold cell culture medium (stored at +2° C. to +8° C.). Subsequently, 1.8 ml of the diluted material was spiked 1:10 with 0.2 ml of pre-diluted* virus stock suspension to a calculated titer of 2.0 and 3.0 $\log_{10}$ [$TCID_{50}$/ml]. After mixing, samples were drawn and titrated immediately. As a control, 1.8 ml of the respective cold cell culture medium (stored at +2° C. to +8° C.) was spiked the very same way with pre-diluted virus stock suspension before titration.

* The appropriate cell culture medium [BT-medium for BT cells (BVDV), A9-medium for A9 cells (MMV)] was used for pre-dilution of virus stock suspensions.

Sampling Plan

Virus Titrations

The following acceptance ranges apply for sample drawing: after 1 day of storage (±1 hour), after 2 to 6 days of storage (±2 hours), after 7 to 13 days of storage (±3 hours), after 14 to 20 days of storage (±4 hours), and after 21 to 27 days of storage (±5 hours). For Sample codes, see Section 1.1 (Process Scheme).

Samples were immediately titrated without additional storage.

| Control stage | Amount |
| --- | --- |
| Virus stock suspension | 1 × 0.3 ml |
| Virus-spiked starting material | 1 × 2 ml |
| Virus-spiked and filtered starting material | 1 × 3 ml |
| Virus-spiked, pH adjusted and filtered starting material [§] | 1 × 1 ml |

| Control stage | Amount |
|---|---|
| Virus-spiked, pH adjusted and filtered starting material stored at low pH at 30 ± 1° C., as soon as the temperature has reached 29° C., i.e. "0 d" sample §, following storage for 7 d §, 14 d §, 20 d (only MMV) § and 27 d (only MMV) § | 1 × 1 ml each |
| Virus-spiked, pH adjusted and filtered starting material stored at low pH at 30 ± 1° C., following storage for 20 d and 27 d (only BVDV) §, titrated by TCID50 assay as well as by bulk titration | 1 × 6 ml each |
| pH Hold control: pH 7.0 ± 0.1, at 30 ± 1° C. | 1 × 5 ml |
| Temperature Hold control: pH 4.9 ± 0.1 §, at +2° C. to +8° C. | 1 × 5 ml |
| Combined pH and Temperature Hold control: pH 7.0 ± 0.1, at +2° C. to +8° C. | 1 × 5 ml |

§ Samples were immediately diluted 1:3.16 with the respective cold cell culture medium before titration.

Determination of Cytotoxicity

Samples were immediately titrated without additional storage.

| Control stage | Amount (for each cell line and each run) |
|---|---|
| Virus stock suspension | 1 × 0.3 ml |
| Mock-spiked and filtered starting material "SM Filt." | 1 × 3 ml |
| Mock-spiked pH adjusted and filtered starting material § "SM pH Filt." | 1 × 1 ml |

§ Samples were immediately diluted 1:3.16 with the respective cold cell culture medium before titration.

Determination of Interference

| Control stage | Amount |
|---|---|
| Virus stock suspension | 1 × 0.3 ml |
| Mock-spiked, pH adjusted (pH 4.9 ± 0.1) and filtered Subcuvia NG intermediate, , diluted 1:3.16 with the respective cold cell culture medium, spiked 1:10 with pre-diluted VSS to a calculated liter of 2.0 $\log_{10}[TCID_{50}/ml]$ | 1 × 1 ml |
| Mock-spiked, pH adjusted (pH 4.9 ± 0.1) and filtered Subcuvia NG intermediate, , diluted 1:3.16 with the respective cold cell culture medium, spiked 1:10 with pre-diluted VSS to a calculated titer of 3.0 $\log_{10}[TCID_{50}/ml]$ | 1 × 1 ml |
| Cold cell culture medium spiked 1:10 with pre-diluted VSS to a calculated titer of 2.0 $\log_{10}[TCID_{50}/ml]$ | 1 × 2 ml |
| Cold cell culture medium spiked 1:10 with pre-diluted VSS to a calculated titer of 3.0 $\log_{10}[TCID_{50}/ml]$ | 1 × 2 ml |

§ Samples were immediately diluted 1:3.16 with the respective cold cell culture medium before titration.

Determination of Biochemical Parameters

Samples were drawn from each unspiked control run only and stored at +2 to +8° C. until analysis.

| Control stage | Parameter | Amount (incl. back-up samples) |
|---|---|---|
| Starting material before spiking[1] | Molecular size distribution "SM - MSD" Cellulose Acetate Electrophoresis "SM - CAE" | 2 × 1 ml |
| Spiked starting material after low pH storage at 30° C. ± 1° C., for 20 days[2] | Molecular size distribution "20 d - MSD" Cellulose Acetate Electrophoresis "20 d - CAE" | 2 × 1 ml |
| Spiked starting material after low pH storage at 30° C. ± 1° C., for 27 days[3] | Molecular size distribution "27 d - MSD" | 2 × 1 ml |

[1] Data generated during production of 2 "Scale-Up"-lots as well as of the custom-made material (Lot. No IGSC64) were also taken into account for evaluation of the downscaled process.
[2] Data generated during production of 2 "Scale-Up"-lots were also taken into account for evaluation of the downscaled process.
[3] With regard to the developmental stage of the product it seems unlikely that data of biochemical parameters after a 28 days storage period were available.

Results and Discussion

The efficacy and robustness of the storage at low pH and elevated temperature of Subcuvia NG as a dedicated inactivation step for both lipid- and non-lipid-enveloped viruses, was investigated with BVDV and MMV, using a downscaled laboratory model of this step. Validation parameters and biochemical parameters were defined and measured in the down-scaled process, and by comparison of the results with the conditions of the manufacturing process the equivalence of the two processes was established.

Results for Validation and Biochemical Parameters

Validation Parameters

The validity of the down-scaled procedure was verified by determination of the parameters critical for virus inactivation, i.e., the pH of the process material, the temperature during low pH storage and the time of storage.

pH Value Before Storage at Low pH and Elevated Temperature

The pH of the spiked process material was measured and adjusted to 4.9±0.1 in all runs, as required and was therefore within the limits specified in the Study Plan. The pH values determined after storage are discussed in Section 4.1.2 (Other Process and Biochemical Parameters).

Temperature Profile

To investigate the robustness of the storage step at low pH and elevated temperature against temperature variations, the temperature was decreased from 30° C.±1° C. to 25±1° C. for 6 hours once every week of storage. The temperature was always within the ranges specified in the Study Plan. However, in the first and in the second week of storage, the decrease in temperature to 25±1° C. for 6 hours was erroneously performed twice per week, i.e., during day 0 and 4 in the first week and during day 7 and 10 in the second week. As this incident shifted the run profile to a worse scenario with respect to virus inactivation, the robustness of virus inactivation was even more extensively investigated than originally intended.

Storage Time

The duration of the storage at low pH and at elevated temperature is not specified for the manufacturing process of Subcuvia NG. Depending on the outcome of the current study, there are several options: one option for the duration of the storage time is 21 to 22 days; a second option may be approximately 28 days. To investigate the efficacy and robustness of the low pH treatment under conditions less favorable for virus inactivation all downscaled runs were performed below the lower limits of the possible storage time; i.e., for 20 days±4 hours for the first option and storage for 27 days±5 hours for the second option. The spiked intermediate was stored at low pH and elevated temperature for 26 days+22 hours (MMV, both runs) and for 27 days+1 hour (BVDV, both runs). In order to investigate virus clearance after 3 weeks of storage, samples for virus titration were drawn after 20 days+1 hour of storage for MMV and after 20 days+2 hours for BVDV.

The storage time was within the specified limits for the down-scale, i.e., 20 days±4 hours, and 27 days±5 hours in all runs, which is below the currently considered lower limits of storage time in manufacturing.

Other Process and Biochemical Parameters pH after Low pH Storage

Following low pH storage, the pH value was measured again directly as well as according to the method recommended by the European Pharmacopoeia (EP), i.e., dilution to 1% protein with 0.9% NaCl solution. The pH measured by direct measurement after the treatment was close to the pH value before low pH storage; i.e., the differences ranged from −0.07 to +0.04 (pH after minus pH before storage). The pH measured according to the EP method was always 0.2 to 0.3 higher compared to the direct measurement method. This slight increase of the pH values when using the EP method is typical for these two different methods in determination of the pH. This fact is also considered in the specified limits at manufacturing scale, where the limits for the pH after low pH treatment are 4.4 to 4.9 when determined by direct measurement and 4.6 to 5.1 when determined by the EP method.

Molecular Size Distribution (MSD)

The molecular size distribution (by HPLC analysis) was investigated before and after storage for the two unspiked control runs. The test results were compared to three "Scale-Up" lots, produced during the developmental stage of Subcuvia NG and to the custom made material IGSC64 (14% as well as 20% protein concentration). Lot IGSC64, which is also designated as a "Scale-Up" lot was not subjected to an storage at low pH and elevated temperature in manufacture, as not enough material was available for this step. All results compared well to each other. Values for Molecular Size Distribution, especially percentage of IgG Monomers, were close to those observed in the "Scale Up" runs. For the second control run, where the concentration of IgG monomers after storage was a few percentage points lower, it is noted that already the material before storage had a comparatively low concentration of IgG monomers, which also applies for the material tested within the "Scale-Up" process. Thus, the molecular size distribution data support the equivalence of the down-scale with the large-scale process.

Purity of Gammaglobulin

Purity of gammaglobulin (by CA-electrophoresis) of samples from the two unspiked control runs were determined and compared to the results obtained from two "Scale-Up" lots and from the custom made material IGSC64 (14% as well as 20% protein concentration, values only before low pH treatment, for explanation see above). All values determined for the purity of gammaglobulin during the down-scaled process compared well to the results obtained for the "Scale Up" lots and were within the assay accuracy (the relative standard deviation is 1.5%). These results demonstrate the comparability of the down scaled to the manufacturing process.

Results for Virus Titration

Cytotoxicity

Cytotoxicity of intermediates obtained before storage at low pH and elevated temperature was investigated in control runs using mock-spiked material adjusted to the respective pH as described for the virus spiked runs. The mock-spiked process intermediates before and after pH adjustment showed only a very weak cytotoxic effect on the cells used in all two runs, except in run 2 on the BT cells, where the pH adjusted intermediate showed no cytotoxic effect from the $1.0 \log_{10}$ dilution and beyond. No significant differences in cytotoxicity were noticed for the virus-spiked runs.

Interference Testing

Results from interference testing show no significant interference of the sample matrix with the detection of low titers of BVDV and MMV: Differences in virus titers between the spiked cell culture medium controls and the spiked Subcuvia NG intermediates were between $-1.0 \log_{10}$ to $0.1 \log_{10}$, which is within the accuracy of the virus titration assay. Thus, titers obtained during the virus inactivation runs were not distorted by interference effects and represent the actual titer of the sample.

Virus Inactivation

Two runs were performed with each of the viruses BVDV and MMV, i.e. run 1 at 13.5% protein concentration, and run 2 at 20.9% protein concentration. Both runs were performed at pH 4.9±0.1 and at 30±1° C., where the temperature was decreased to 25±1° C. for a minimum of 6 hours once per week. Comparison of the results of the two runs revealed no significant differences in virus inactivation kinetics between the two runs performed at the upper and the lower limit of the possible protein concentration of Subcuvia NG.

Employing conditions least favorable for virus inactivation, i.e. the lower limits of storage time and temperature, as well as upper limits of pH, significant inactivation of BVDV after 20 days±4 hours of storage and complete inactivation of all the virus that could be spiked into the respective Subcuvia NG intermediate after 27 days±5 hours of storage was demonstrated for BVDV, irrespective of the conditions investigated. In both runs residual infectivity from BVDV could be still be detected on day 20. However, all BVDV was inactivated to below the limit of detection by the end of the 27 day storage. The reduction factors for MMV demonstrate a substantial contribution of this process step to the viral safety of the product, also with regard to non-lipid enveloped viruses. Individual virus titers and reduction factors for the viruses used are discussed in more detail further below. In addition, graphical illustrations of the virus inactivation kinetics are given for each virus following the respective results-table.

BVDV

BVDV was inactivated nearly to the limit of detection (run 1) or to the limit of detection (run 2) by day 20 of storage, providing for reduction factors of $5.3 \log_{10}$ and $5.5 \log_{10}$ in runs 1 and 2, respectively. After 27 days of storage all BVDV spiked into the Subcuvia NG intermediate was inactivated to below the limit of detection for both runs, with reduction factors of $>6.6 \log_{10}$ and $>6.5 \log_{10}$ in runs 1 and 2, respectively. No significant differences could be observed in the inactivation kinetics of the two runs. Both intermediates in run 1 (with 13.5% protein concentration)] and run 2 (with 20.9% protein concentration) showed comparable inactivation kinetics.

The low pH treatment at elevated temperature demonstrated effective inactivation of BVDV after storage for 20 days±4 hours, with a calculated mean reduction factor of $5.4 \log_{10}$. After 27 days of storage at low pH and elevated temperature, complete inactivation of BVDV to below the limit of detection was achieved, where a mean reduction factor of $>6.6 \log_{10}$ was calculated.

MMV

For MMV reduction factors of 2.9 $\log_{10}$ and 3.1 $\log_{10}$ were calculated for run 1 and 2, respectively, after 20 days of storage at low pH and elevated temperature. The calculated mean reduction factor is 3.0 $\log_{10}$. After 27 days of low pH treatment reduction factors of 3.4 $\log_{10}$ and 3.7 $\log_{10}$ were obtained, where the calculated mean reduction factor is 3.6 $\log_{10}$. These reduction factors demonstrate a substantial contribution of this process step to the viral safety profile of the manufacturing process with regard to Parvoviruses, which are very resistant towards physicochemical inactivation. The virus inactivation kinetics in both runs was biphasic, with faster inactivation during the first 7 days and somewhat slower inactivation during the following three weeks.

Hold Controls

To investigate the mechanism of virus inactivation, i.e., whether mediated by pH or by temperature or by a combination of the two, three hold controls were kept under the respective conditions.

Titration of the "Combined Hold Control" (pH 7.0±0.1) that were kept at 2° C. to 8° C. for 27 days±5 hours resulted for both viruses investigated in a virus titer comparable with the virus spiked starting material, except for MMV in run 2, where a small loss in titer (1.6 $\log_{10}$) was observed.

Storage at 30±1° C. and pH 7.0±0.1 ("pH Hold Control") showed that the lipid enveloped virus BVDV was very sensitive to storage at elevated temperature. BVDV was inactivated by 4.6 $\log_{10}$ in both runs. Also, the non-lipid-enveloped virus MMV was inactivated by 3.3 and 3.8 $\log_{10}$, in run 1 and run 2, respectively.

Titration of the "Temperature Hold Controls" (t HC) after a 27 days±5 hours storage at low pH and at 2° C. to 8° C. resulted for both viruses investigated in a virus titer comparable with the virus spiked starting material. These results demonstrate that BVDV as well as MMV were resistant to storage at low pH in the range of 4.4 to 4.9 at low temperature.

Taken together, the results of the three Hold Controls suggest that:

Temperature would be the most significant factor for the inactivation of BVDV, with some contribution of the low pH (based on the fact that the control at 30±1° C. and neutral pH was substantially, but not completely inactivated after 27 days).

For inactivation of MMV, temperature seemed to be the only relevant factor as the virus titers of the low pH kinetic samples after 27 days was virtually identical with the control at neutral pH and 30° C.

SUMMARY AND CONCLUSION

In the course of the present study, a down-scaled model of the storage at low pH and elevated temperature in the manufacture of Subcuvia NG was established and its equivalence to the manufacturing procedure was demonstrated by determination of several process parameters. In addition, a comparison of biochemical parameters of intermediates from the down-scaled model and the manufacturing process further supported the equivalence of both processes, indicating that the reduction factors obtained during the down-scale are also valid for the large scale. To investigate the robustness with regard to virus inactivation, the impact of different protein concentrations of Subcuvia NG was investigated, the pH of the spiked starting material was adjusted to the upper limit compared to the manufacturing process, and the impact of periodic decreases in temperature was investigated. The virus reduction factors and the inactivation kinetics obtained in the current study demonstrate that the lipid-enveloped virus BVDV is effectively and robustly inactivated by storage at low pH and elevated temperature within 27 days. Also, after storage at low pH and elevated temperature for 20 days a significant inactivation of BVDV with a mean calculated reduction factor of 5.4 $\log_{10}$ was achieved for BVDV. The calculated mean reduction factors for the parvovirus model MMV, i.e., 3.0 $\log_{10}$ after 20 days of storage and 3.6 $\log_{10}$ after 20 days of storage, show that this process step further contributes to the viral safety of the manufacturing process with regard to small non lipid-enveloped DNA viruses for high physicochemical resistance [2], for an storage time of 20 as well as of 27 days.

Both protein concentrations investigated showed the same inactivation kinetics for MMV and BVDV, suggesting that the impact of protein concentration on the virus inactivation capacity is not significant for concentrated Immunoglobulin solutions and the viruses BVDV and MMV.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing a concentrated immunoglobulin G (IgG) composition, comprising:
   (A) concentrating IgG in a solution to a first concentration of from 2% to 10% (w/v) by ultrafiltration using a first ultra-/diafiltration system comprising a first ultrafiltration membrane having a first nominal molecular weight cut off and a first surface area;
   (B) diafiltering the IgG in the solution against a diafiltration buffer using the first ultra-/diafiltration system comprising the first ultrafiltration membrane; and
   (C) concentrating the IgG in the solution to a second concentration of greater than 20% (w/v) by ultrafiltration using a second ultra-/diafiltration system comprising a second ultrafiltration membrane having a second nominal molecular weight cut off and a second surface area, wherein the second surface area of the second ultrafiltration membrane is less than the first surface area of the first ultrafiltration membrane.

2. The method of claim 1, wherein the surface area of the second ultrafiltration membrane is no more than a tenth of the surface area of the first ultrafiltration membrane.

3. The method of claim 1, wherein the first nominal molecular weight cut off of the first ultrafiltration membrane and the second nominal molecular weight cut off of the second ultrafiltration membrane are separately 100 kDa or less.

4. The method of claim 2, wherein the first nominal molecular weight cut off of the first ultrafiltration membrane and the second nominal molecular weight cut off of the second ultrafiltration membrane are separately 100 kDa or less.

5. The method of claim 1, wherein the first nominal molecular weight cut off of the first ultrafiltration membrane and the second nominal molecular weight cut off of the second ultrafiltration membrane are separately 50 kDa or less.

6. The method of claim 2, wherein the first nominal molecular weight cut off of the first ultrafiltration membrane and the second nominal molecular weight cut off of the second ultrafiltration membrane are separately 50 kDa or less.

7. The method of claim 1, wherein the first nominal molecular weight cut off of the first ultrafiltration membrane and the second nominal molecular weight cut off of the second ultrafiltration membrane are both 50 kDa.

8. The method of claim 2, wherein the first nominal molecular weight cut off of the first ultrafiltration membrane and the second nominal molecular weight cut off of the second ultrafiltration membrane are both 50 kDa.

9. The method of claim 1, wherein the first nominal molecular weight cut off of the first ultrafiltration membrane and the second nominal molecular weight cut off of the second ultrafiltration membrane are both 30 kDa.

10. The method of claim 2, wherein the first nominal molecular weight cut off of the first ultrafiltration membrane and the second nominal molecular weight cut off of the second ultrafiltration membrane are both 30 kDa.

11. The method of claim 1, wherein the diafiltration buffer comprises from 0.2 M to 0.3 M glycine and a pH of 4.2±0.1.

12. The method of claim 2, wherein the diafiltration buffer comprises from 0.2 M to 0.3 M glycine and a pH of 4.2±0.1.

13. The method of claim 8, wherein the diafiltration buffer comprises from 0.2 M to 0.3 M glycine and a pH of 4.2±0.1.

14. The method of claim 10, wherein the diafiltration buffer comprises from 0.2 M to 0.3 M glycine and a pH of 4.2±0.1.

15. The method of claim 1, further comprising, after concentrating the IgG in the solution using the first ultra-/diafiltration system:
- (D) washing the first ultrafiltration membrane by re-circulating a post-wash buffer through the first ultra-/diafiltration system, thereby recovering IgG lost from the solution; and
- (E) concentrating the recovered IgG using the second ultra-/diafiltration system comprising the second ultrafiltration membrane.

16. The method of claim 2, further comprising, after concentrating the IgG in the solution using the first ultra-/diafiltration system:
- (D) washing the first ultrafiltration membrane by re-circulating a post-wash buffer through the first ultra-/diafiltration system, thereby recovering IgG lost from the solution; and
- (E) concentrating the recovered IgG using the second ultra-/diafiltration system comprising the second ultrafiltration membrane.

17. The method of claim 8, further comprising, after concentrating the IgG in the solution using the first ultra-/diafiltration system:
- (D) washing the first ultrafiltration membrane by re-circulating a post-wash buffer through the first ultra-/diafiltration system, thereby recovering IgG lost from the solution; and
- (E) concentrating the recovered IgG using the second ultra-/diafiltration system comprising the second ultrafiltration membrane.

18. The method of claim 10, further comprising, after concentrating the IgG in the solution using the first ultra-/diafiltration system:
- (D) washing the first ultrafiltration membrane by re-circulating a post-wash buffer through the first ultra-/diafiltration system, thereby recovering IgG lost from the solution; and
- (E) concentrating the recovered IgG using the second ultra-/diafiltration system comprising the second ultrafiltration membrane.

* * * * *